US005667975A

United States Patent [19]
Dykstra et al.

[11] Patent Number: 5,667,975
[45] Date of Patent: Sep. 16, 1997

[54] METHOD OF FLUORESCENT DETECTION OF NUCLEIC ACIDS AND CYTOSKELETON ELEMENTS USING BIS-DICATIONIC ARYL FURANS

[75] Inventors: Christine C. Dykstra, Auburn, Ala.; Richard R. Tidwell, Chapel Hill, N.C.; David W. Boykin; W. David Wilson, both of Atlanta, Ga.

[73] Assignee: The University of North Carolina

[21] Appl. No.: 485,381

[22] Filed: Jun. 7, 1995

Related U.S. Application Data

[63] Continuation-in-part of Ser. No. 238,766, May 6, 1994.

[51] Int. Cl.$^6$ .................................................. C12Q 1/68
[52] U.S. Cl. .................. 435/6; 435/4; 435/5; 435/7.1; 435/7.2; 435/29; 435/40.5; 435/810; 435/501; 536/23.1; 536/24.1; 536/24.3; 536/24.31; 536/24.32; 536/24.33; 935/77; 935/78
[58] Field of Search ............................ 435/4, 5, 6, 7.1, 435/7.2, 29, 40.5, 810; 436/501; 536/23.1, 24.1, 24.3-33; 935/77, 78

[56] References Cited

U.S. PATENT DOCUMENTS

| | | | |
|---|---|---|---|
| 4,324,794 | 4/1982 | Tidwell et al. | 424/273 B |
| 4,397,863 | 8/1983 | Tidwell et al. | 424/274 |
| 4,619,942 | 10/1986 | Tidwell et al. | 514/415 |

FOREIGN PATENT DOCUMENTS 2839989  4/1980  Germany .

OTHER PUBLICATIONS

Dykstra, C., et al, Synthesis and Characterization of a Novel Series of Aromatic Dicationic Furans With DNA-Specific Fluorescence Properties, pp. 1–7, (1994).
Wilson, W., et al, The Search for Structure–Specific Nucleic Acid–interactive Drugs: Effects of Compound Structure on RNA versus DNA Interaction Strength. Biochemistry, 32:4098 (1992).
Bottiroli, et al., DNA Double Staining for a Fluorescence Energy Transfer Study of Chromatin in Liver Cells, Cell Biophysics, 15:249 (1989).
Grossgebauer, A New Fluorescence Technique for Staining of Mononuclear Phagocytes, Blut, 39:281–283 (1979).
Rayburn, et al., Short Note—Estimating Percentage Consitutive Heterochomatin by Flow Cytometry, Experimental Cell Research, 198:175–178 (1992).
Babu, A., et al., Expression of Heterochromatin by Restriction Endonuclease Treatment and Distamycin A/DAPI Staining of Indian Muntjac (Muntiacus muntjak) Chromosomes, Cytogenet Cell Genet 41:96 (1986).
Parolin, C., et al., The Effect of the Minor Groove Binding Agent DAPI (2–amidino–diphenyl–indole) on DNA-Directed Enzymes: an Attempt to Explain Inhibition of Plasmid Expression in Escherichia coli, FEMS Microbiology Letters 68:341 (1990).

Buys, C.H.C.M., et al., A Comparison of the Effect of 5–Bromodeoxyuridine Substitution on 33258 Hoechst– and DAPI–Fluorescence of Isolated Chromosomes by Bivariate Flow Karyotyping, Histochemistry 84:462 (1986).
Mohan, S., et al., Flexibility of DNA In 2:1 Drug–DNA Complexes—Simultaneous Binding of Two DAPI Molecules to DNA, J. Biomolecular Structure and Dynamics 9:695 (1991).
Kapuscinski, J., Interactions of Nucleic Acids with Fluorescent Dyes: Spectral Properties of Condensed Complexes, J. Histochemistry and Cytochemistry 38:1323 (1990).
Jansen, K., et al., Binding of DAPI Analogue 2,5–Bis(4–Amidinophenyl)furan to DNA, Biochemistry 32:6605 (1992).
Bonaly, J., et al., A Flow Cytometric Study of DNA Staining In Situ in Exponentially Growing and Stationary Euglena gracilis, Cytometry 8:42 (1987).
Heng, H.H.Q., et al., Modes of DAPI Banding and Simultaneous in situ Hybridization, Chromo. 326–332 (1993).
Bonne, D., et al., 4',6–Diamidin–2–phenylindole, A Fluorescent Probe for Tubulin and Microtubules, J. Biological Chemistry 260:2819 (1985).
Das, B.P., et al., 1,4–Bis(4–guanylphenylethyl)benzenes as Potential Antitrypanosomal Agents, J. Pharmaceutical Sciences 71: 465 (1982).
Das, B.P., et al., Synthesis and Antiprotozoal Activity of 2,5–Bis(4–guanylphenyl)furans, J. Medicinal Chemistry 10:531 (1977).
Das, B.P., et al., Synthesis and Antitrypanosomal Activity of Some Bis(4–guanylphenyl) Five– and Six–Membered Ring Heterocycles, J. Medicinal Chemistry 23:578 (1980).
Das, B.P., et al., Synthesis and Antiprotozoal Activity of 2,5–Bis(4–guanylphenyl)thiophenes and – pyrroles, J. Medicinal Chemistry 20:1219 (1977).
Yamamoto, K., et al., DNA Recognition and Novel Site–Specific Alkylation by Duocarmycin A with Distamycin A, Biochemistry 32:1059 (1993).
Miyakawa, I., et al., Isolation of Morphologically Intact Mitochondrial Nucleoids from the Yeast, Saccharomyces cerevisiae, J. Cell Science 88:431 (1987).
Myc, A., et al., DNA Stainability in Aneuploid Breast Tumors: Comparison of Four DNA Fluorochromes Differing in Binding Properties, Cytometry 13:389 (1992).
Dam, O., et at., Trypanocide Diamidine mit drei isolierten Ringsystemen, Anal. Chem. 11:160 (1975).
Wilson, W.D., et al., The Effects of Ligand Structure on Binding Mode and Specificity in the Interaction of Unfused Aromatic Cations with DNA. Molecular Basis of Specificity in Nucleic Acid–Drug Interactions, pp. 331–353 (1990).
Wilson, W.D., et al., Molecular Factors that Control the Nucleic Acid Binding Mode Selection by Unfused Aromatic Cations. Structure and Function: Nucleic Acids 1:83 (1992).

Primary Examiner—Ardin H. Marschel
Attorney, Agent, or Firm—Bell, Seltzer, Park & Gibson

[57] ABSTRACT

Disclosed is a method of fluorescent detection of a nucleic acid. The method comprises contacting to the nucleic acid a bis-dicationic aryl furan and exposing the nucleic acid to light at a frequency to induce fluorescence of the compound. A method for fluorescent detection of cytoskeleton elements, and novel bis-dicationic aryl furan compounds are also disclosed.

23 Claims, No Drawings

METHOD OF FLUORESCENT DETECTION OF NUCLEIC ACIDS AND CYTOSKELETON ELEMENTS USING BIS-DICATIONIC ARYL FURANS

RELATED APPLICATIONS

This application is a continuation-in-part application of U.S. Ser. No. 08/238,766 filed May 6, 1994, for "Method of Fluorescent Detection of Nucleic Acids and Cytoskeleton Elements Using Bis-Dicationic Aryl Furans" by Christine C. Dykstra, et al.

The present invention was made with Government support under Grant Number 1UO1-AI3363 from the National Institutes of Health. The Government has certain rights to this invention.

FIELD OF THE INVENTION

The present invention relates to a method for binding and detecting nucleic acids and cytoskeleton elements. More specifically, the invention relates to a method for fluorescent detection of nucleic acids and cytoskeleton elements using bis-dicationic aryl furan compounds.

BACKGROUND OF THE INVENTION

Many types of sample analysis rely upon the fluorescence properties of a stain. Fluorescence occurs when a molecule excited by light of one wavelength returns to the unexcited (ground) state by emitting light of a longer wavelength. The exciting and emitted light, being of different wavelengths, can be separated from one another using optical filters. Fluorescence has been used to visualize certain molecules (and hence structures) by light microscopy for many years, and is also used in other analytical techniques, such as flow cytometry.

The type of fluorescent probe used in fluorescent analysis can be divided into two broad categories, those used to label covalently other probes (often antibodies) and those whose distribution or fluorescence reflects their environment and hence particular properties of a cell. Among the latter, fluorescent compounds that bind specifically to nucleic acids or to cytoskeleton structures or elements are particularly important.

A variety of fluorescent probes are known. For example, propidium and ethidium stains are available. These compounds, however, bind to both deoxyribonucleic acid (DNA) and double stranded ribonucleic acid (RNA). Thus, RNA has to be removed if DNA is to be measured.

4',6-diamidino-2-phenylindole (DAPI) is also used as a DNA stain for numerous applications in cytology, nucleic acid biophysical analysis, and flow cytometry. DAPI binds preferentially to the DNA minor groove at AT-rich DNA sequences but also intercalates at GC and mixed GC/AT sequences, and significantly binds RNA. W. D. Wilson, et al., "The Effects of Ligand Structure on Binding Mode of Unfused Aromatic Cations with DNA" in *Molecular Basis of Specificity in Nucleic Acid-Drug Interactions*, Klumar Academic Publishers, Amsterdam (1990), pps. 331–353; W. D. Wilson, et al., *Biochemistry* 32, 4098–4104 (1993). DAPI also binds other cellular components, such as tubulin, resulting in RNA and tubulin staining.

A number of aryldiamidines have been synthesized in the past with value as anti-protozoal agents. B. P. Das and D. W. Boykin, *J. Med. Chem.* 20, 531–536 (1977). Like DAPI, 2,5-bis(4-amidinophenyl)furan (also referred to as 2,5-bis (4-guanylphenyl)furan) binds preferentially to the DNA minor groove at AT-rich DNA sequences but also interacts with GC and mixed GC/AT sequences. W. D. Wilson, et al. (1990), supra; W. D. Wilson, et al. (1993), supra.

Another stain used in fluorescent analysis applications is the bis-benzimide Hoechst 33258. Loontiens et al have suggested that Hoechst 33258, a closely related molecule, binds to GC-rich sequences via a self-association complex in the major groove of DNA. F. G. Loontiens, et al., *Biochemistry* 29, 9029–9039 (1990). This agent also has a significant association with RNA. Wilson, et al. (1993), supra. Thus, as with DAPI and 2,5-bis(4-amidinophenyl)furan, significant staining of non-DNA elements can result with Hoechst 33258.

SUMMARY OF THE INVENTION

A first aspect of the present invention provides novel compounds of Formula (I):

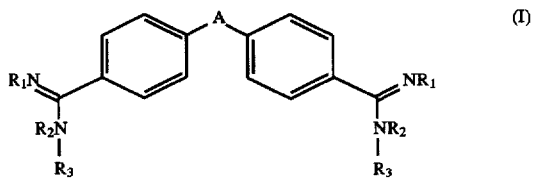

wherein:

$R_1$ and $R_2$ are each independently selected from the group consisting of H, lower alkyl, alkoxyalkyl, cycloalkyl, aryl, alkylaryl, hydroxyalkyl, aminoalkyl, or alkylaminoalkyl, or $R_1$ and $R_2$ together represent a $C_2$ to $C_{10}$ alkyl, hydroxyalkyl, or alkylene or $R_1$ and $R_2$ together are:

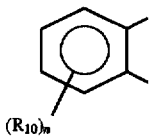

wherein n is a number from 1 to 3, and $R_{10}$ is H or —$CONHR_{11}NR_{15}R_{16}$ wherein $C_{11}$ is lower alkyl and $R_{15}$ and $R_{16}$ are each independently selected from the group consisting of H and lower alkyl; and $R_3$ is H, hydroxy, lower alkyl, cycloalkyl, aryl, alkylaryl, alkoxyalkyl, hydroxycycloalkyl, alkoxycycloalkoxy, hydroxyalkyl, aminoalkyl or alkylaminoalkyl;

A is a heterocyclic aromatic group selected from the group consisting of:

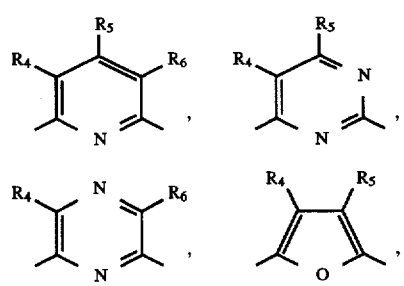

-continued

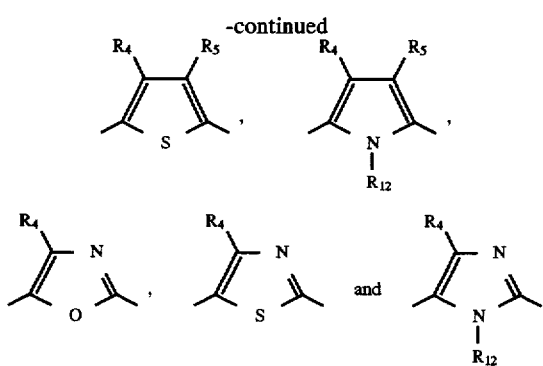

wherein R₄, R₅, and R₆ are each independently selected from the group consisting of H, lower alkyl, halogen, aryl, arylalkyl, aminoalkyl, aminoaryl, oxyalkyl, oxyaryl, or oxyarylalkyl;

$R_{12}$ is hydrogen, lower alkyl, hydroxy, aminoalkyl or alkylaminoalkyl, or a physiologically acceptable salt thereof.

The present invention also provides novel compounds of Formula (II):

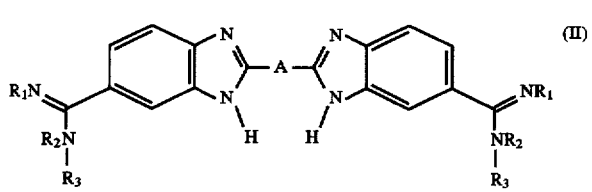

(II)

wherein:

$R_1$ and $R_2$ are each independently selected from the group consisting of H, lower alkyl, alkoxyalkyl, cycloalkyl, aryl, alkylaryl, hydroxyalkyl, aminoalkyl, or alkylaminoalkyl, or $R_1$ and $R_2$ together represent a $C_2$ to $C_{10}$ alkyl, hydroxyalkyl, or alkylene or $R_1$ and $R_2$ together are:

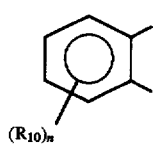

wherein n is a number from 1 to 3, and $R_{10}$ is H or —$CONHR_{11}NR_{15}R_{16}$ wherein $C_{11}$ is loweralkyl and $R_{15}$ and $R_{16}$ are each independently selected from the group consisting of H and lower alkyl; and $R_3$ is H, hydroxy, lower alkyl, cycloalkyl, aryl, alkylaryl, alkoxyalkyl, hydroxycycloalkyl, alkoxycycloalkoxy, hydroxyalkyl, aminoalkyl or alkylaminoalkyl;

A is a heterocyclic aromatic group selected from the group consisting of:

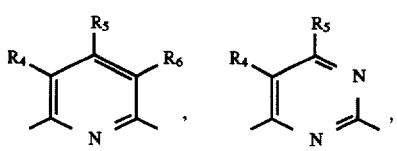

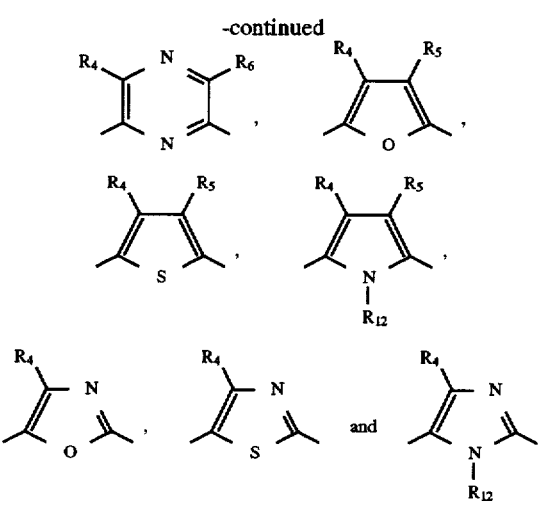

wherein R₄, R₅, and R₆ are each independently selected from the group consisting of H, lower alkyl, halogen, aryl, arylalkyl, aminoalkyl, aminoaryl, oxyalkyl, oxyaryl, or oxyarylalkyl;

$R_{12}$ is hydrogen, lower alkyl, hydroxy, aminoalkyl or alkylaminoalkyl, or a physiologically acceptable salt thereof.

In one preferred embodiment of the invention for compounds of Formula (I), $R_1$ and $R_2$ together are:

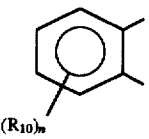

wherein n is a number from 1 to 3, and $R_{10}$ is H or —$CONHR_{11}NR_{15}R_{16}$ wherein $R_{15}$ and $R_{16}$ are each independently selected from the group consisting of H and lower alkyl; and each of $R_3$, $R_4$ and $R_5$ are H.

In another preferred embodiment of the invention for compounds of Formula (I) and (II), $R_1$, $R_3$, $R_4$, $R_5$, and $R_6$ are each H and $R_2$ is lower alkyl.

In yet another preferred embodiment of the invention for compounds of Formula (II), $R_1$ and $R_2$ together represent a $C_2$ to $C_4$ alkylene, $R_3$, $R_4$, $R_5$, and $R_6$ are H and $R_{12}$ is H or lower alkyl. In one aspect of this embodiment of the invention, $R_1$ and $R_2$ together represent

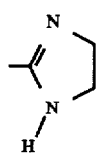

and $R_3$ is H.

In another aspect of this embodiment of the invention, $R_1$ and $R_2$ together represent

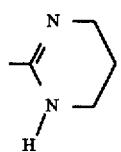

and $R_3$ is H.

In yet another preferred embodiment of the invention for compounds of Formula (II), each of $R_1$, $R_2$ $R_3$, $R_4$, $R_5$ and $R_6$ are H and $R_{12}$ is H or lower alkyl.

In yet another preferred embodiment of the invention for compounds of Formula (II), A is:

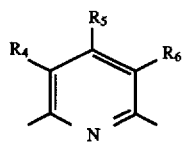

wherein $R_4$, $R_5$, and $R_6$ are each H.

In another preferred embodiment of the invention for compounds of Formula (II), A is:

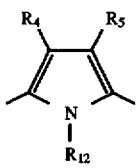

wherein $R_4$ and $R_5$ are each H and $R_2$ is H or lower alkyl.

In another preferred embodiment of the invention for compounds of Formula (II), A is:

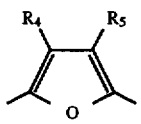

wherein $R_4$ and $R_5$ are each H.

A second aspect of the present invention is a method of fluorescent detection of nucleic acids. The method comprises contacting to the nucleic acid a compound according to Formula (I) and/or (II), and exposing the nucleic acid to light to induce fluorescence of the compound of Formula (I) and/or (II).

A third aspect of the invention is a method for the selective fluorescent detection of DNA in a nucleic acid mixture containing DNA and RNA. The method comprises the steps of (a) contacting a nucleic acid mixture with a compound according to Formula (I) and/or (II), and (b) exposing the nucleic acid mixture to light to induce fluorescence of the compound of Formula (I) and/or (II).

Yet another aspect of the present invention is a method for the fluorescent detection of a microtubular structure. The method comprises contacting to the microtubular structure a compound according to Formula (I) and/or (II), and exposing the microtubular structure to light to induce fluorescence of the compound of Formula (I) and/or (II).

Still another aspect of the present invention is a method for the simultaneous fluorescent detection of a first cellular structure and a second cellular structure in a cell, wherein said first cellular structure and said second cellular structure are different. The method includes (a) contacting the cell with a first fluorescent compound and a second fluorescent compound. The first and second fluorescent compounds are structurally different from each other, but each of the fluorescent compounds has a structure according to Formula (I) and/or (II). The first fluorescent compound selectively binds to the first structure and the second compound selectively binds to the second structure. In addition, the first and second fluorescent compounds have different fluorescent emission spectra. After the cell is contacted with the first and second fluorescent compounds, (b) the cell is exposed to light to induce fluorescence of both the first and second fluorescent compounds, so that the first cellular structure and the second cellular structure fluoresce at different fluorescent emission spectra.

As yet another aspect of the present invention, a kit is provided for the fluorescent detection of a cellular structure. The kit includes (a) a compound according to Formula (I) and/or (II), and (b) a solvent in an amount sufficient to form a mixture of a nucleic acid labelled with the compound of Formula (I) and/or (II), when the compound is contacted to a sample including a nucleic acid.

The foregoing and other objects and aspects of the present invention are explained in detail in the specification set forth hereinbelow.

DETAILED DESCRIPTION OF THE INVENTION

Disclosed herein are compounds useful in a method for the fluorescent detection of a nucleic acid. The compounds comprise compounds of Formula (I) below:

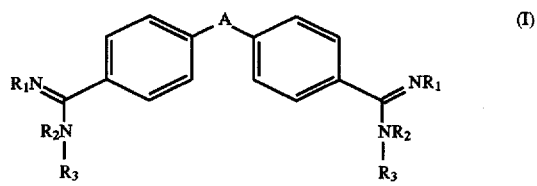

(I)

wherein $R_1$ and $R_2$ are each independently selected from the group consisting of H, lower alkyl, alkoxyalkyl, cycloalkyl, aryl, alkylaryl, hydroxyalkyl, aminoalkyl, or alkylaminoalkyl, or $R_1$ and $R_2$ together represent a $C_2$ to $C_{10}$ alkyl, hydroxyalkyl, or alkylene or $R_1$ and $R_2$ together are:

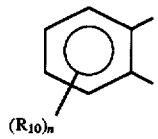

wherein n is a number from 1 to 3, and $R_{10}$ is H or —CONHR$_{11}$NR$_{15}$R$_{16}$ wherein $C_{11}$ is lower alkyl and $R_{15}$ and $R_{16}$ are each independently selected from the group consisting of H and lower alkyl. Preferably, $R_{10}$ is H. $R_{10}$ may be positioned at any of the C-2, C-3, C-4, or C-5 positions in the ring. Preferably, $R_{10}$ is positioned at the C-3 position.

Compounds useful in a method for the fluorescent detection of a nucleic acid in accordance with the present invention also comprise compounds of Formula (II) below:

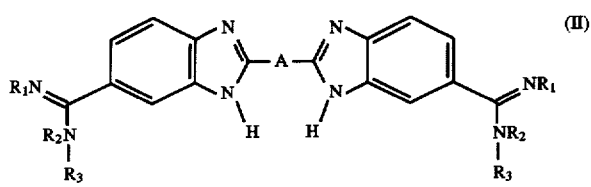
(II)

wherein $R_1$ and $R_2$ are each independently selected from the group consisting of H, lower alkyl, alkoxyalkyl, cycloalkyl, aryl, alkylaryl, hydroxyalkyl, aminoalkyl, or alkylaminoalkyl, or $R_1$ and $R_2$ together represent a $C_2$ to $C_{10}$ alkyl, hydroxyalkyl, or alkylene or $R_1$ and $R_2$ together are:

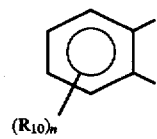
$(R_{10})_n$ wherein n is a number from 1 to 3, and $R_{10}$ is H or —$CONHCR_{11}NR_{15}R_{16}$ wherein $C_{11}$ is lower alkyl and $R_{15}$ and $R_{16}$ are each independently selected from the group consisting of H and lower alkyl. Preferably, $R_{10}$ is H. $R_{10}$ may be positioned at any of the C-2, C-3, C-4, or C-5 positions in the ring. Preferably, $R_{10}$ is positioned at the C-3 position.

In one preferred embodiment of the invention, for compounds in accordance with Formula (I), $R_1$ and $R_2$ together are:

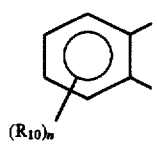
$(R_{10})_n$ wherein n and $R_{10}$ are as defined above.

In another preferred embodiment for compounds in accordance with Formula (II), $R_1$ and $R_2$ together represent a $C_2$ to $C_{10}$ linear, saturated alkylene. More preferably, $R_1$ and $R_2$ together represent a $C_2$ to $C_5$ linear, saturated alkylene.

In one aspect this embodiment of the invention, $R_1$ and $R_2$ together represent

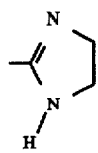

In another aspect of this embodiment of the invention, $R_1$ and $R_2$ together represent

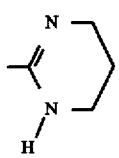

In another preferred embodiment of the invention for compounds in accordance with Formula (II), each of $R_1$ and $R_2$ is H.

In yet another preferred embodiment of the invention for compounds of Formula (I) and (II), $R_1$ is H and $R_2$ is lower alkyl, preferably isopropyl.

$R_3$ may be selected from the group consisting of H, hydroxy, lower alkyl, cycloalkyl, aryl, alkylaryl, alkoxyalkyl, hydroxycycloalkyl, alkoxycycloalkoxy, hydroxyalkyl, aminoalkyl or alkylaminoalkyl. Preferably, $R_3$ is H or alkylhydroxy of the formula —$R_{14}OH$, wherein $R_{14}$ is lower alkyl. Preferably, $R_{14}$ is —$(CH_2)_2$—.

A is a heterocyclic aromatic group selected from the group consisting of:

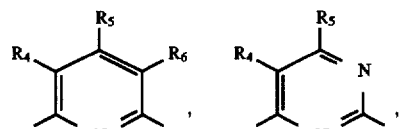

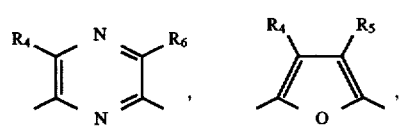

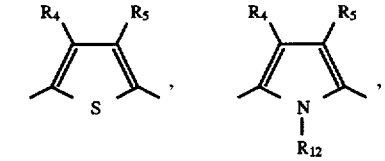

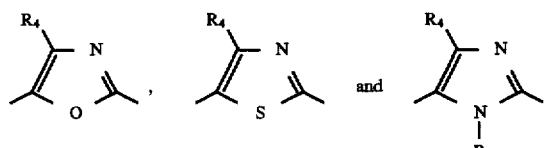

The foregoing groups representing A may be ortho, meta or para substituted with $R_4$ and $R_5$.

$R_4$ may be selected from the group consisting of H, lower alkyl, halogen, oxyalkyl, oxyaryl, or oxyarylalkyl. Preferably, $R_4$ is H or lower alkyl.

$R_5$ may be selected from the group consisting of H, lower alkyl, halogen, oxyalkyl, oxyaryl, or oxyarylalkyl. Preferably, $R_5$ is H.

$R_{12}$ may be selected from the group consisting of hydrogen, lower alkyl, hydroxy, aminoalkyl or alkylaminoalkyl. Preferably $R_{12}$ is H or lower alkyl.

In one preferred embodiment for compounds of Formula (I), A is

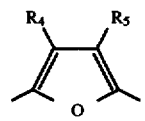

wherein $R_4$ and $R_5$ may be defined as above, but preferably, $R_4$ is H, and $R_5$ is $OCH_3$ or $O(C_6H_4)R$, wherein R is H or lower alkyl. More preferably, R is lower alkyl, and preferably methyl.

In another preferred embodiment of the invention, for compounds of Formula (II), A is

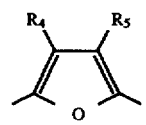

wherein $R_4$ and $R_5$ may be defined as above, but preferably, $R_4$ and $R_5$ are each H.

In yet another preferred embodiment of the invention for compounds of Formula (II), A is:

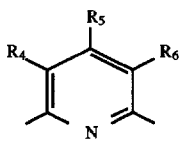

wherein $R_4$, $R_5$, and $R_6$ are each H.

In yet another preferred embodiment of the invention for compounds of Formula (II), A is:

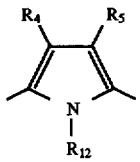

wherein $R_4$ and $R_5$ are each H and $R_{12}$ is H or lower alkyl.

As used herein, the term "lower alkyl," refers to C1 to C6 linear or branched alkyl, such as methyl, ethyl, propyl, butyl, isopropyl, sec-butyl, and tert-butyl, butyl, pentyl, isopentyl, and hexyl. The term "cycloalkyl" as used herein refers to C3 to C6 cyclic alkyl, such as cyclopropyl, cyclobutyl, cyclopentyl, and cyclohexyl. The term "aryl" as used herein refers to C3 to C10 cyclic aromatic groups such as phenyl, naphthyl, and the like, and includes substituted aryl groups such as tolyl. The term "hydroxyalkyl" as used herein refers to C1 to C4 linear or branched hydroxy-substituted alkyl, i.e., —$CH_2OH$, —$(CH_2)_2OH$, etc. The term "aminoalkyl" as used herein refers to C1 to C4 linear or branched amino-substituted alkyl, wherein the term "amino" refers to the group NR'R", wherein R' and R" are independently selected from H or lower alkyl as defined above, i.e., —$NH_2$, —$NHCH_3$, —$N(CH_3)_2$, etc. The term "alkoxyalkyl" as used herein refers to C1 to C6 linear or branched alkoy, such as methoxy, ethoxy, propyloxy, butyloxy, isopropyloxy, and t-butyloxy.

Compounds which are representative of the novel compounds of Formula (I), and which are preferred in the methods of the present invention include, but are not limited to 2,5-bis(4-amidinophenyl)furan;

2,5-bis[4-(4,5-dihydro-1H-imidazoyl-2-yl)phenyl]furan;

2,5-bis[4-1,4,5,6-tetrahydropyrimidin-2-yl)phenyl]furan;

2,5-bis[4-(4,5,6,7-tetrahydro-1H-1,3-diazepin-2-yl)phenyl]furan;

2,5-bis[4-(N-isopropyl amidino)phenyl furan;

and physiologically acceptable salts thereof.

Compounds which are representative of the novel compounds of Formula (II), and which are preferred in the methods of the present invention include, but are not limited to 2,5-bis(5-amidino-2-benzimidazolyl)pyrrole;

2,5-bis-[5-(2-imidazolinyl)-2-benzimidazolyl]pyrrole;

2,6-bis[5-(2-imidazolinyl)-2-benzimidazolyl]pyridine;

1-methyl-2,5-bis(5-amidino-2-benzimidazolyl)pyrrole;

1-methyl-2,5-bis[5-(2-imidazolyl)-2-benzimidazolyl] pyrrole;

1-methyl-2,5-bis[5-(1,4,5,6-tetrahydro-2-pyrimidinyl)-2-benzimidazolyl]pyrrole;

2,6-bis(5-amidino-2-benzimidazoyl)pyridine;

2,6-bis[5-(1,4,5,6-tetrahydro-2-pyrimidinyl)-2-benzimidazolyl]pyridine;

2,5-bis(5-amidino-2-benzimidazolyl)furan;

2,5-bis[5-(2-imidazolinyl)-2-benzimidazolyl]furan;

2,5-bis(5-N-isopropylamidino-2-benzimidazolyl)furan;

and physiologically acceptable salts thereof.

The method of the present invention is carried out by contacting or mixing a nucleic acid in a substantially pure solution thereof, or in a biological sample containing the nucleic acid with a compound of Formula (I) and/or (II) above and then exposing the biological sample to light to induce fluorescence of the compound of Formula (I) and/or (II). The step of exposing the biological sample to light to induce the fluorescence of the compounds of Formula (I) and/or (II) allows analysis of the sample, i.e., detection of the presence of nucleic acid components contained therein. The method of the invention is useful in, for example, light microscopy, flow cytometry, karyotype analysis, nucleic acid detection and quantitation, electrophoresis, and the like.

The compounds of the invention bind to nucleic acids in the sample, and thus are suitable for staining any biological sample suspected of containing nucleic acids. As used herein, the term "nucleic acid" refers to both deoxyribonucleic acid (DNA) and ribonucleic acid (RNA). Any nucleic acid may be stained, including chromosomal and extrachromosomal nucleic acids (e.g., a plasmid, an RNA virus, etc). As a result, the presence of nucleic acids in biological samples can be observed by techniques known in the art for detecting nucleic acids in a sample by fluorescent detection a of compound bound thereto, including light microscopy, confocal light microscopy, flow cytometry, and the like.

Exemplary samples suitable for staining in accordance with the present invention typically are obtained in the form of a sample of a biological fluid or biological tissue. Those skilled in this art will appreciate that samples can be drawn from any number of biological sources from which useful diagnostic information can be obtained. Suitable biological fluids include, but are not limited to, blood, saliva, urine, milk, lymph fluid, and oral, nasal, and bronchial mucosa. Suitable tissue samples include, but are not limited to, tissue biopsy samples, such as from kidney, liver, lymph node, or other organs, and skin and other soft tissue samples (e.g., muscle). Specimens taken from subjects may be stained directly, or provided as a growth cultured from the specimen. The appropriate selection of the biological specimen and appropriate culture techniques will be readily apparent to one skilled in the art. The sample can also be a substantially pure solution of the nucleic acid to be detected, i.e., a solution of an intracellular component isolated from a specimen as described above.

Samples may be collected from both plant and animal species. Animal species include both human and non-human species (e.g., dog, cat, rat, cow, horse, sheep, monkey, etc.). Other types of cells, such as bacteria, fungi, protozoa, and other unicellular organisms, can also be treated in accordance with the present invention. Thus, cells which can be used include both eukaryotic and prokaryotic.

Typically, cells are stained by incubation under appropriate conditions with the fluorescent compound according to Formula (I) and/or (II). For example, staining by the compounds according to Formula (I) and/or (II) can be achieved by following standard protocols known in the art for DAPI staining as described in O. Miller, *Principles and Practices in Medical Genetics* (Longman Group Limited, New York 1983) and D. Silvonen, ACT *Cytogenetic Lab Manual* (University of California, San Francisco 1980). Alternatively, the sample can be stained using standard protocols for bis-benzimide staining as is also known in the art. See, e.g., *Human Cytogenetics*, Volume 1, Constitutional Analysis, pg 113 (D. Rooney and B. Czepulkowski, Eds., IRL press at Oxford University Press).

The sample is contacted or mixed with an amount of a compound of Formula (I) and/or (II) to bind the compound with nucleic acid in the sample. Since one molecule of the compound of Formula (I) and/or (II) generally binds to four base pairs double stranded nucleic acid, any amount sufficient to produce a detectable signal may be used. Thus, the proportion or ratio of the amount of a compound of Formula (I) and/or (II) to a target to be detected may be about 1:4, 1:8, 1:16, 1:32 or more, depending among other things on how the target is to be detected. If desired, excess amounts of the compound can optionally be washed away after staining. As will be appreciated by the skilled artisan, washing is not required for analytical techniques wherein the sample is provided as a substantially pure solution of the nucleic acid as described above, analyzed using, for example, a fluorimeter.

The compound can be provided in an aqueous solution, and the contacting step can be carried out by simply immersing the sample with the solution. There is, however, no need to store the solution in the dark to preserve the stability of the compounds, as has been reported as necessary for DAPI. Such a solution can have a minimum final concentration of about 0.01 micromolar (μM), although the solution can have a final concentration between about 0.01 and 5, 10, or 25 micromolar or more. The duration of contact between the sample and the compound can vary widely depending on the contacting technique, but is generally between about 30 seconds and two hours, and is preferably between about 1 and 15 minutes, when the sample is immersed in a solution in the concentrations described above.

The sample can also be stained using combinations of fluorochromes. Thus, fluorescence from compounds according to Formula (I) and/or (II) and from other compounds can be detected simultaneously for such compounds fluorescent detection at different wavelengths. As will be appreciated by the skilled artisan, when more than one label is used, care should be taken to select fluorochromes with maximum emission wavelengths or spectra that do not overlap. In addition, a combination of fluorochromes can be selected to amplify the fluorescent signal using fluorescent energy transfer techniques. Also as will be appreciated by the skilled artisan, when more than one fluorochrome is used, care should be taken to select fluorochromes which do not chemically interact with one another or with the compounds according to Formula (I) and/or (II).

In the application of the method of the invention, it may be advantageous to modify the compounds of Formula (I) and/or (II) to remove DNA binding affinity, without removing convenient conjugation sites to which other entities may attach. One suitable entity to which compounds of Formula (I) and/or (II) may be conjugated includes oligonucleotides of both DNA and RNA. Such conjugates of the compound of Formula (I) and/or (II) may be useful for anti-sense reagents, probes for hybridization studies, bandshift assays of DNA-protein complexes, or for primers for fluorescent DNA sequencing and PCR applications. Additionally, the compounds of Formula (I) and/or (II) may be conjugated to numerous reagents for in situ labeling studies. Exemplary reagents include antibodies for immunohistochemistry, and size marker molecules to measure volume. The compounds of Formula (I) and/or (II) may also be conjugated to reagents for the purpose of forming substrates for measurement of enzyme activities that either gain or lose fluorescence upon enzyme activity, e.g., proteases, phosphatases, kinases, antibiotic inactivation, nucleases, and carbohydrates. The conjugated compounds of Formula (I) and/or (II) may or may not have to be unconjugated in situ to produce fluorescence. In other words, the conjugated compounds of Formula (I) and/or (II) may retain fluorescence despite conjugation, or may fluoresce upon cleavage from the conjugate.

The exposing step of the method of the invention can be carried out by known techniques suitable for inducing the compound of Formula (I) and/or (II) to produce a detectable signal. Generally this will comprise exposing the biological sample to ultraviolet light at a frequency which will induce fluorescence of the compound of Formula (I) and/or (II) (e.g., 210–380 nm). The only limitation is that the intracellular component to be detected, i.e., nucleic acid, is not destroyed by the light frequency and/or intensity.

As will be appreciated by the skilled artisan, the wavelength selected to induce fluorescence of the compound is known in the art as the "excitation maximum," i.e., that wavelength which is absorbed by a molecule and excites that molecule to a higher electronic state. As noted above, in the invention, the excitation wavelength is in the ultraviolet range. When the molecule passes from the higher to a lower electronic state, the molecule emits a type of visible radiation, i.e., fluorescence, of a wavelength referred to as the "emission maximum." It is the fluorescence that is detected in the present invention. The detectable signal emitted by the compound can be detected using techniques known in the art, for example by observation with the human eye, using electronic means for detecting a generated wavelength, and the like.

Advantageously, the wavelength of fluorescence is sufficiently removed from that of the exciting light to allow good separation of the two wavelengths by optical filters. Filtered light can be used, for example, to select the desired wavelength of exciting light on the input side, and/or to select the appropriate range of emission wavelengths for measurement of fluorescence peak or maxima.

Another aspect of the invention relates to methods for binding cytoskeleton elements of a cell in a sample and detecting the presence of the same. In this aspect of the method of the invention, a compound according to Formula (I) and/or (II) above or a physiologically acceptable salt thereof is contacted or mixed with a cytoskeleton element in a substantially pure solution thereof, or in a biological sample containing the cytoskeleton element. As described above, after mixing the compound of Formula (I) and/or (II) with a cytoskeleton element, the sample is exposed to light at a frequency which induces fluorescence of the compound of Formula (I) and/or (II) so as to allow analysis of the sample, i.e., detection of the presence of cytoskeleton elements components contained therein. This aspect of the invention is useful in, for example, light microscopy, including confocal light microscopy, biochemical assays, and the like. This aspect of the method of the invention can be conducted as described above in more detail with regard to the fluorescent detection of nucleic acids.

As used herein, the term "cytoskeleton elements" refers to protein fibers comprising the structural framework of a cell. The present invention is particularly preferred for use with microtubular structures as the cytoskeleton element, which is particularly sensitive to this method. As will be appreciated by the skilled artisan, tubulin is a major protein of microtubules. Thus this aspect of the invention can provide techniques for determining disruption of the polymerization of tubulin in forming microtubular structures.

For light microscopy, samples are preferably immobilized on a solid support prior to the introduction of the compounds of the invention (the staining reagents). Any solid support can be used, with exemplary solid supports including microscope slides, wall surfaces of reaction wells, test tubes, and cuvettes, and beads. The solid support can be formed of any material known to be suitable to those skilled in this art, including glass, polystyrene, polyethylene, polypropylene, and cross-linked polysaccharides. Preferably, the sample is fixed to a glass microscope slide. The sample can be fixed to the solid support by any suitable procedure, such as air-drying or chemical or heat treatment, that does not interfere with subsequent observation of the sample. It is preferred that the slide be immobilized in such a manner that it can be observed by light microscopy.

For light microscopy, the sample can be stained with the compounds according to Formula (I) and/or (II) by following standard protocols known in the art for DAPI or bis-benzimide staining, as noted above. Advantageously, the sample is washed after staining to remove excess amounts of the compound of Formula (I) and/or (II) so as to remove background interference and to improve resolution of the sample. The staining process is initiated by contacting the sample with a compound according to Formula (I) and/or (II) in an amount sufficient to bind nucleic acid or cytoskeleton elements in the sample, for example, by immersing the sample with an aqueous solution of the compound. The amount of the compound of Formula (I) and/or (II) and duration of contacting can be as described above.

The thus prepared sample slides can be analyzed using known fluorescent techniques, such as fluorescent microscopy. For example, the sample can be viewed using a photomicroscope equipped with an ultraviolet (UV) source such as a mercury or xenon lamp and appropriate filters, and the images photographed using conventional techniques. The cells are illuminated with a UV light source, which is the source of excitation, and must be capable of producing specific wavelengths that can be used to excite the fluorescent compounds of the invention.

The method of the invention can be used with other analytical techniques, such as flow cytometry. Flow cytometry is a technique for making rapid measurements on particles or cells as they flow in a fluid stream one by one through a sensing point. The aim of sample preparation is to produce a suspension of disperse particles stained in a specific way which will pass through the system without disrupting the smooth flow of fluid or blocking tubes or orifices.

Sample preparation is in accordance with known techniques for flow cytometry. To stain the sample, the sample is contacted with a compound of Formula (I) and/or (II) following the protocols set forth above with regard to concentrations and duration of contact. The sample is contacted with the compound of Formula (I) and/or (II) prior to injecting or delivering the sample to the fluid stream of the flow cytometry system to provide a suspension of disperse particles. As will be appreciated by the skilled artisan, body fluids, such as blood containing individual cells, can be stained and processed directly on the flow cytometer to measure absolute cellular content of the macromolecule in question. Preparation of solid tissues can be direct, i.e., simple chopping and teasing of the organ followed by sieving and density gradient centrifugation. Other tissues can require enzymatic digestion.

To deliver particles of a random three dimensional suspension one by one to a specific point in space intersected by the illuminating beam, generally the sample suspension is injected into the center of an enclosed channel through which liquid is flowing. The cells pass through the detection point, where the cell is illuminated. As with light microscopy, the light is the source of excitation, and the light source must be capable of producing specific wavelengths that can be used to excite the fluorescent compounds of the invention. The scattered and fluorescent light generated by cells passing through the illuminating beam is collected by photodetectors which convert the photon pulses into electronic signals. Further electronic and computational processing results in graphic display and statistical analysis.

Compounds of Formula (I) employed in carrying out the present invention may be prepared in accordance with techniques known to those skilled in the art (see, e.g., B. P. Das and D. W. Boykin, *J. Med. Chem.* 20, 531–536 (1977), the entire disclosure of which is hereby incorporated by reference), by the techniques exemplified in Examples 1–4 and 6–8 below, or variations thereof which will be apparent to those skilled in the art. In addition, the compounds can be synthesized by a variation of the method set forth in B. P. Das and D. W. Boykin, supra, as exemplified in Example 5 below.

The compounds of Formula (I) are prepared generally as indicated in the reaction scheme below by: (a) cyclodehydrative furanization of 1,4-diketones (1) according to the procedure taught by R. E. Lutz, et al., *J. Am. Chem. Soc.* 56, 2698 (1934) to form 2,5-bis-(4-bromophenyl)furan (2); (b) nitrilization of 2,5-bis(4-bromophenyl)furan (2) using $Cu_2(CN)_2$ to produce the corresponding bis-nitrile 2,5-bis-(4-cyanophenyl)furan (3); and (c) conversion of the bis-nitrile (3) to the bis-dicationic aryl furan of Formula (I) (4) by conversion into intermediate imidate esters followed by reaction of these intermediates with ammonia or the appropriate diamine, for example, ethylenediamine, 1,3-propanediamine, etc., as exemplified in the Examples below. Steps (a) and (b) are described in more detail in Example 1, and step (c) is described in more detail in Examples 2–8.

REACTION SCHEME

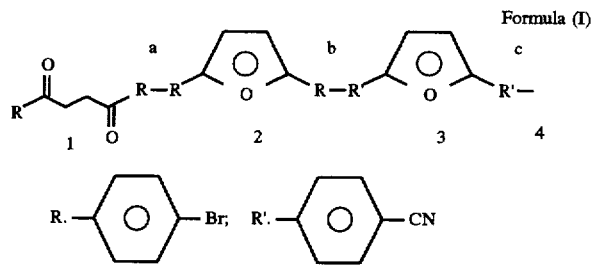

Alternatively, step (c) above can be substituted by a thermolysis step, wherein the bis-nitrile (3) is transformed into a compound of Formula (I) using heat to fuse a diamine salt, i.e., amine hydrochloride, directly with the bis-nitrile, as exemplified by Example 5 below. This alternative procedure is limited to the preparation of compounds of Formula (I) wherein $R_1$ and $R_2$ together from a cyclic moiety.

The compounds of Formula (II) may also be prepared according to methods known in the art, particularly in light of the disclosure and examples set forth below. According to one method, the compounds of Formula (II) can be prepared by condensation of an appropriate heterocyclic compound (i.e., pyrrole, pyridine, furan, etc.) dicarboxaldehyde (for example pyrrole-2,5-dicarboxaldehyde) which can be prepared according to the teaching of T. Cresp, et al., *J. Chem. Soc. Perkins Tran.* 1, 2961 (1973) with the appropriate diaminophenyl compound (for example diaminobenzamidine prepared according to T. Fairley, et al., *Med. Chem.* 36, 1746 (1993). The condensation reaction can be conducted according to the method of S. Kumar, et al., *Indian J. Chem* 20B, 254 (1981).

The diaminophenyl compounds can be prepared, for example, by reduction of nitro groups of 3,4- dinitrobromobenzene to form 3,4-diaminobromobenzene. Nitrilization of this compound to the corresponding 3,4-diaminonitrilebenzene can be conducted by reacting copper (I) cyanide with the thus prepared 3,4-dinitrobromobenzene in refluxing DMF according to the standard techniques. See, J. Spychala, et al., *European J. Med. Chem.* 29:363 (1994). The nitrile can then be converted to the imidate ester by the Pinner methodology, according to B. Das, et al., *J. Med. Chem.* 20, 1219 (1977). The imidate ester can be converted into compounds of Formula (II), for example, by reaction with ammonium or the appropriate aminoalkane or diaminoalkane (such as ethylenediamine, propylenediamine, etc.), to form an amidino group, an imidazolinyl group, an 1,4,5, 6-tetrahydro-2-pyrimidinyl group, respectively. The bis-nitrile can also be converted to the bis-dicationic compound by fusion of the nitrile directly with the hydrochloride salt of the appropriate diamine by thermolysis. This technique is particularly useful for the preparation of compounds wherein the $R_1$ and $R_2$ groups together form a cyclic alkyl.

The compounds of Formula II above can also be prepared by first preparing an appropriate intermediate, such as 2,5-bis(5-bromo-2-benzimidazolyl)pyrrole by the base promoted condensation, for example, of 1-bromo-3,4-diaminobenzene and pyrrole-2,5-dicarboxaldehyde, according to the method of S. Kumar, et al., supra. The intermediate can then be obtained by nitrilization followed by imidate ester formation and conversion into the corresponding amidino as described above.

As indicated, the compounds used in the present invention may be present as physiologically acceptable salts (e.g., salts which are not so unduly disruptive of the sample so that the compound is not capable of being detected). Such salts include the glauconite, lactate, acetate, tartrate, citrate, maleate, furmarate, phosphate, borate, nitrate, sulfate, and hydrochloride salts. The salts of the present invention may be prepared, in general, by reacting two equivalents of the amidine base compound with the desired acid, in solution. After the reaction is complete, the salts are crystallized from solution by the addition of an appropriate amount of solvent in which the salt is insoluble.

The spectroscopic properties and utilities of the compounds according to Formula (I) and/or (II) as fluorescent dyes are similar to DAPI and Hoechst 33258. Compounds according to Formula (I) and/or (II), however, can bind double-stranded DNA strongly and with high specificity, with essentially no binding to RNA. For example, 2,5-bis [4-(4,5,6,7-tetrahydro-1H-1,3-diazepin-2-yl)phenyl]furan has essentially no detectable affinity for RNA. In addition, the compounds of Formula (I) and/or (II) can emit a blue color of a slightly different wavelength than that emitted by DAPI, and there can be less light scatter than that observed with DAPI. This can result in delineation of more detail.

The present invention can be advantageously provided to the user in the form of a kit. Typically a staining kit comprises reagents in amounts sufficient to carry out the aforementioned steps, i.e., a compound according to Formula (I) and/or (II). The reagents should be provided in a form suitable for long-term storage such as a crystalline powder or an aqueous solution. In addition, the kit will generally include, inter alia, vials for storing the reagents, mixing vessels, and an instruction sheet that sets forth the aforementioned steps. The reagents may also include ancillary agents such as buffering agents and the like. The kit may further include, where necessary, agents for reducing background interference in a test, control reagents, apparatus for conducting a test, and the like.

The present invention will be further illustrated by the following non-limiting examples, in which "g" means grams, "mg" means milligrams, "μg" means micrograms, "mmol" means millimoles, "h" means hours, "ml" means milliliter, "M" means molar, "mM" means millimolar, "μM" means micromolar, "UV" means ultraviolet, "HCl" means hydrogen chloride, "mp" means melting point, "HCN" means hydrocyanic acid and "°C." means degrees Celsius. Except where noted otherwise, the experimental detail relating to the synthesis of compounds according to Formula (I) is the synthetic procedure in accordance with that set forth in B. P. Das and D. W. Boykin, *J. Med. Chem.* 20, 531–536 (1977).

EXAMPLE 1

Preparation of Precursor Compounds 2,5-Bis(p-bromophenyl) furan.

A literature procedure as known in the art for preparation of trans-di-p-bromobenzoylethylene from bromobenzene and fumaryl chloride was employed. J. B. Conant and R. E. Lutz, *J. Am. Chem. Soc.* 47, 881 (1925). The ethylene compound was reduced with Zn-HOAc to prepare 1,4-di-p-bromophenyl-1,4-butanedione. E. Campaigne and W. O. Foye, *J. Org. Chem.* 17, 1405 (1952). The saturated 1,4-diketone (7.9 g, 0.02 mol) was suspended in 80 mL of $AC_2O$ and the mixture was heated to reflux. Concentrated $H_2SO_4$ (4–5 drops) was added and refluxing was continued for 5 min. The solution was poured into water-ice (1 L), stirred well, and filtered: crude yield 7 g (93%). Recrystallization from acetic acid gave 5.6 g (75%), mp 198°–199° C. (lit. (R. E. Lutz and W. M. Eisner, *J. Am. Chem. Soc.* 56, 2698 (1934)) mp 200°–201° C.).

2,5-Bis(p-cyanophenyl)furan.

A mixture of 7.5 g (0.02 mol) of 2,5-bis-(4-bromophenyl) furan and 4 g (0.045 mol) of Cu(CN) in 45 mL of quinoline was refluxed for 2 h. The mixture was poured into 300 mL of dilute HCl solution (caution, HCN is liberated) and filtered. The solid was washed with $H_2O$, dilute NaOH, dilute HCl, and again with $H_2O$. The solid bis-nitrile was dissolved in acetone, filtered to remove inorganic residue, and passed through a short alumina column to remove traces of copper salts. The copper salts must be removed since they carry over to the bis-amidines from which they are difficult to purify. A convenient method to detect the presence of copper salts is a flame test. Evaporation of the eluent from the alumina column and recrystallization from ethanol gave 3.5 g (65%), mp 294°–295° C.

EXAMPLE 2

Preparation of 2,5-Bis(4-amidinophenyl)furan dihydrochloride 2,5-Bis(4-cyanophenyl)furan (3 g, 0.011 mol) (prepared as described in Example 1) in a mixture of 100 mL of dioxane and 25 mL of absolute ethanol was saturated with dry HCl gas at 5° C. The solution was placed in a pressure bottle and shaken for 3 days (room temperature). An intermediate product, an imidate ester hydrochloride, precipitated as a yellow solid, was filtered and dried under vacuum at room temperature overnight. The IR spectra of the imidate ester hydrochloride was free of adsorption for nitrile and it was used directly without further characterization. A suspension of the imidate ester hydrochloride (3.5 g) in 100 mL of absolute ethanol was saturated at 5° C. with anhydrous ammonia. The suspension (pressure bottle) was shaken for 3 days at room temperature. The reaction mixture was filtered and the solid was dried and dissolved in warm absolute ethanol (ca. 1.5 L). The solution was acidified with anhydrous HCl at 5° C., concentrated under vacuum at room temperature, and 2.5 g (60%) of yellow crystals were obtained. Recrystallization from absolute ethanol gave mp 400°–401° C. dec.

EXAMPLE 3

Preparation of 2,5-Bis[4-(4,5-dihydro-1H-imidazol-2-yl) phenyl]furan

A solution of an imidate ester hydrochloride intermediate synthesized as described in Example 2, 2.1 g (0.005 mol), and 0.6 g (0.01 mol) of ethylenediamine in 50 mL of absolute ethanol was refluxed overnight. The solid which formed was filtered and recrystallized from absolute ethanol saturated with anhydrous HCl to yield 2,5-Bis[4-(2-imidazolinyl)phenyl]furan, 1.9 g (90%), mp 409°–410° C. dec.

EXAMPLE 4

Preparation of 2,5-Bis[4-(1,4,5,6-tetrahydropyrimidin-2-yl) phenyl]furan

In a similar manner as set forth in Example 3, an imidate ester hydrochloride synthesized as described above in Example 2 was reacted with 1,3-propanediamine to yield (90%) of the 2,5-Bis[4-(1,4,5,6-tetrahydropyrimidin-2-yl) phenyl]furan, mp 430°–431° C. dec.

EXAMPLE 5

Preparation of 2,5-Bis[4-(4,5-dihydro-1H-imidazol-2-yl) phenyl]furan dihydrochloride dihydrate This compound was obtained by an alternate method from 2,5-bis(4-cyanophenyl)furan. For this reaction dinitrile (0.5 g, 1.9 mmole), ethylenediamine dihydrochloride (4.9 g, 37 mmole), and ethylenediamine (2.5 ml, 37 mmole) were used. A mixture of the dinitrile, ethylenediamine dihydrochloride, and ethylenediamine was maintained at 300°–310° C. for 10 minutes and then dissolved in hot water. Yellow crystals separated on cooling. The compound was recrystallized from boiling water. Yield, 208 mg (24%). TLC ($CHCl_3$:$CH_{OH}$.25% $NH_4OH$=11:4:1, one spot), mp >360° C. Anal. Calculated for: $C_{22}H_{20}N_4O.2H_2O$ (465.37): C, 56.78; H, 5.60; N, 12.04. Found: C, 56.69; H, 5.63; N, 12.07. $^1$H-NMR (DMSO-$d_6$, TMS), δ4.01 (s, 8H), 7.45 (s, 2H), 8.08 (d, 4H, J=8.3 Hz), 8.15 (d, 4H, J=8.3 Hz), 8.15 (d, 4H, J=8.3 Hz), 10.50 (brs, 4H). 13C-NMR (DMSO-$d_6$, TMS), δ45.5, 113.2, 121.6, 125.3, 130.1, 135.8, 153.4, 165.8. IR (KBr): v 3412, 3123, 2971, 1608, 1580, 1491, 1367, 1287, 1033, 850, 745, 673. MS, m/z: 356 (free base).

EXAMPLE 6

Preparation of 2,5-Bis[4-(4,5,6,7-tetrahydro-1H-1,3-diazepin-2-yl)phenyl]furan dihydrochloride hemiheptahydrate The bis-methoxyethanol imidate ester (1 g, 0.002 mole), and 1,4-diaminobutane (0.5 g, 0.0057 mole) in 10 ml of 1,2-dimethoxyethane were refluxed for 2 days. The solvent was removed in vacuum and water was added. The precipitate was filtered, washed with water and dried in a vacuum oven (m.p. >300° C.). The free base reaction product of the bis-methoxyethanol imidate ester and 1,4-diaminobutane was converted into the hydrochloride (m.p. >300° C.) by hydrogen chloride in methanol. The filtrate was neutralized using 2N sodium hydroxide and another portion of the free base was obtained. The total yield of free base was 51%. Anal. Calculated for $C_{26}H_{28}N_4O.2HCl.3.5H_2O$ (548.50): C, 56.93; H, 6.80; N, 10.22. Obtained: C, 56.99; H, 6.80; N, 10.26. $^1$H-NMR (DMSO-$d_6$), δ2.02 (s, 8H), 3.71 (s, 8H), 7.38 (s, 2H), 7.86 (d, 4H, J=8.3 Hz), 8.04 (d, 4H, J=8.3 Hz), 9.77 (s, 4H). $^{13}$C-NMR ($D_2O$ ($CH_3$)$_3$Si$CH_2CH_2CO_2$Na), δ28.0, 47.0, 113.9, 126.5, 129.7, 131.2, 137.0, 154.5, 167.1. IR (KBr), v 687, 747, 814, 930, 1331, 1364, 1459, 1597, 3008, 3164. MS (EI), m/z (% rel. int.) 412 (100) (free base), 384 (23), 354 (9), 340 (13), 298 (11), 284 (23).

EXAMPLE 7

Preparation of 2,5-Bis{[4-N-isopropyl)-amindino] phenyl}furan

Dry isopropylamine (0.47 g, 0.008 mole) was added to a suspension of an imidate ester as described in Example 2 (1.3 g, 0.003 mole) in 45 ml absolute ethanol. Within 0.5 hr the imidate ester dissolved and the mixture of the imidate ester and isopropylamine became colored. After ca. 3 hr a white solid precipitated; the slurry was stirred overnight at room temperature. The solvent was removed under reduced pressure, diluted with water, filtered and washed with water. After the solid was dried, it was recrystallized from an ethanol/ether mixture to yield a white solid 0.9 g (78%); mp 233°–4° C., $^1$H NMR (DMSO-$d_6$)/60° C.) 7.79 (brs, 8H), 7.11 (s, 2H), 6.25 (br, 4H), 3.81 (br, 2H), 1.14 (d, 6H, J=5.9). $^{13}$C NMR (DMSO-$d_6$/60° C.) 152.4, 142.0, 136.6, 130.4, 126.8, 122.8, 108.7, 43.5, 22.8.

EXAMPLE 8

Preparation of 2,5-Bis[4-N-isopropyl)amindino)phenyl] furan dihydrochloride 0.78 g (0.002 mole) of the free base prepared as described in Example 7 was dissolved in 10 ml absolute ethanol and treated with 10 ml of ethanol saturated with hydrogen chloride and warmed for 2 hr. The mixture was reduced in volume to 5 ml. Addition of 20 ml of dry ether produced a bright yellow precipitate which was filtered, washed with 3×5 ml dry ether and dried in vac. at 65° C. for 2 hr to yield 0.8 g (87%). Mp 276°–70° C. (dec). IR (KBr). $^1$H NMR (DMSO-$d_6$) 9.72 (s, 1H) 9.69 (s, 1H), 9.57 (s, 2H), 9.24 (s, 2H), 8.06 (d, 4H, J=8.1), 7.86 (d, 4H, J=8.1), 7.42 (s, 2H), 4.14 (s, 2H, J=6.6), 1.29 (d, 12H, J=6.6). $^{13}$C NMR (DMSO-$d_6$) 161.1, 152.3, 133.6, 129.2, 127.7, 123.5, 111.3, 45.1, 21.1.

Anal. Calculated for: $C_{24}H_{28}N_4O.2HCl.1.25$ $H_2O$: C, 59.57; H, 6.79; N, 11.57. Found: C, 60.00; H, 6.80; N, 11.52.

EXAMPLE 9

Preparation of 2,5-bis[(4-(4,5-dihydro-1H-imidazol-2-yl) phenyl)]-3-(4-tolyloxy)furan 1-(4-tolyloxyl)-1,2-bis(4-bromobenzoyl)ethylene. To a solution of 1,2-dibromo-1,2-di(4-bromobenzoyl)ethane (11.1 g, 0.02 mole) in 35 ml of THF was added a suspension of sodium 4-methyl phenoxide [prepared from 0.92 g (0.04 mole) Na and 4.32 g (0.04 mole) 4-methylphenol in 30 ml THF by refluxing for 4–5 hr]. The yellow mixture was refluxed for 2–3 hr (TLC followed) after which the THF was removed under reduced pressure. The residue was treated with water, and the solid was filtered, washed with water, dried ($Na_2SO_4$), and dissolved in chloroform. The chloroform solution was passed through a silica column (elution with 2–5% ether in hexane). The result was an off white crystalline solid, 4.95 g (50%), mp 137°–8° C. IR (KBr) 3087, 3035, 2868, 1687, 1646, 1587, 1572, 1557, 1502, 1399, 1364, 1194, 1068, 1009, 971, 876, 815, 772, 526. $^1$H NMR (CDCl$_3$/35° C.) 7.92 (d, 2H, J=8.8), 7.65 (d, 2H, J=8.8), 7.55 (d, 2H, J=8.8), 7.48 (d, 2H, J=8.8), 7.27 (d, 2H, J=8.3), 7.11 (d, 2H, J=8.3), 6.32 (s, 1H), 2.4 (s, 3H). $^{13}$C NMR (CDCl$_3$/35° C.) 189.4, 187.6, 168.4, 150.9, 136.6, 136.0, 133.4, 132.3, 131.8, 130.9, 130.3, 129.6, 129.2, 128.2, 120.6, 101.8, 20.95. MS m/e 500 (M$^+$).

2,5-bis(4-Bromophenyl)-3-(p-tolyloxy)furan. A solution of 5.0 g (0.01 mole) 1-(4-tolyloxy)-1,2-bis-(4-bromobenzoyl)ethylene in 10 ml phosphorus trichloride was heated under reflux for 3–4 hr (TLC followed). The excess PCl$_3$ was removed by distillation and the residue was triturated with ice/water (exothermic reaction). The solution was extracted with dichloromethane (75 ml) and the dichloromethane layer was washed with saturated sodium bicarbonate solution, water, and dried (Na$_2$SO$_4$). The solvent was removed under reduced pressure. The residual solid was chromatographed over silica gel using ether:hexane (2:8 to 1:1) as eluant. An off white crystalline solid was obtained, 2.78 g (56%), mp 92°-3° C. IR (KBr) 2923, 2851, 1560, 1506, 1467, 1390, 1209, 1072, 1066, 945, 825, 707, 486. $^1$H NMR (CDCl$_3$/35° C.) 7.69 (d, 2H, J=8.8), 7.46–7.43 (m, 6H), 7.12 (d, 2H, J=8.3), 7.0 (d, 2H, J=8.3), 6.47 (s, 1H), 2.31 (s, 3H). $^{13}$C NMR (CDCl$_3$/135° C.) 150.8, 150.1, 142.8, 139.3, 133.0, 131.9, 131.7, 130.3, 129.1, 128.6, 125.1, 125.0, 121.8, 120.5, 117.1, 102.7, 20.6. MS m/e 484 (M$^+$).

2,5-bis(4-Cyanophenyl)-3-(4-tolyloxy)furan. A mixture of the dibromo compound prepared above (2.5 g, 0.0051 mole) and cuprous cyanide (1.81 g, 0.02 mole) in 8 ml dry N-methyl-2-pyrrolidone was heated at ca. 200° C. under a nitrogen atmosphere for 2.5 hr (TLC followed), cooled, and poured into 200 ml of water. The precipitated solid was filtered, resuspended in 100 ml of water and 100 ml of 10% NaCN was added and the mixture was stirred for 3–4 hr. The solid was filtered, washed with water and placed in a soxlate device using acetone for ca. 24 hr. The acetone extract was reduced in volume and passed through a short column of neutral aluminum, the eluate was evaporated and the resulting solid was recrystallized from CHCl$_3$:ether (2:8) to give a yellow crystalline solid 1.2 g (62%), mp 198°-9° C. IR (KBr) 3067, 2223, 1618, 1303, 1505, 1402, 1220, 1169, 1008, 926, 840, 820, 668, 546 cm$^{-1}$. $^1$H NMR (CDCl$_3$/35° C.) 7.98 (d, 2H, J=8.8), 7.75 (d, 2H, 8.3), 7.68 (d, 2H, J=8.8), 7.65 (d, 2H, J=8.8), 7.19 (d, 2H, J=8.3), 7.05 (d, 2H, J=8.3), 6.66 (s, 1H), 2.36 (s, 3H). $^{13}$C NMR (CDCl$_3$/35° C.) 154.3, 150.3, 145.8, 139.1, 134.0, 133.6, 133.3, 132.7, 132.6, 130.5, 124.2, 123.8, 119.0, 118.6, 117.8, 111.5, 110.0, 104.5, 20.7. Anal. Calcd. for C$_{25}$H$_{16}$N$_2$O$_2$: C, 79.76; H, 4.28; N, 7.44; Found: C, 79.68; H, 4.31; N, 7.39. MS m/e 376 (M$^+$).

2,5-bis[(4-(4,5-dihydro-1H-imidazol-2-yl)phenyl)]-3-(4-tolyloxy)furan. The bis-nitrile prepared above [1 g (0.0026 mole)] was placed in 20 ml absolute ethanol and 50 ml absolute dioxane which was saturated with dry HCl gas at 0° C. The mixture was allowed to stir at room temperature for 4 days. A thick yellow precipitate formed, 100 ml of dry ether was added and the solid was filtered, washed with 100 ml dry ether and dried in vacuo at 25° C. for 5 hr to yield 0.78 g (66%) imidate ester hydrochloride. The imidate ester was resuspended into 25 ml dry ethanol and heated at gentle reflux with 0.31 g (0.0053 mole) ethylenediamine for 12 hr. The excess ethanol was removed by distillation and the residue was treated with water, basified with 1M NaOH (stirring and cooling). The yellow precipitate was filtered, washed with water, dried and recrystallized from boiling ethanol to yield 0.6 g (74%), mp 156°-7° C. IR (KBr) 3218, 2927, 2862, 1609, 1506, 1398, 1218, 1105, 987, 848, 669 cm$^{-1}$. $^1$NMR (DMSO-d$_6$/50° C.) 7.94–7.84 (m, 8H), 7.21 (d, 2H, J=8.3), 7.12 (s, 1H), 7.08 (d, 2H, J=8.79), 3.63 (s, 4H), 3.62 (s, 4H), 2.28 (s, 3H). $^{13}$C NMR (DMSO-d$_6$/50° C.) 163.0, 162.9, 154.3, 150.4, 142.8, 139.0, 132.4, 130.8, 130.4, 130.1, 129.7, 128.5, 127.5, 127.4, 123.2, 122.6, 116.5, 104.0, 49.3, 49.2, 19.9. MS m/e 462 (M$^+$).

The free base [0.5 g (0.001 mole)] in 10 ml ethanolic HCl was heated at reflux 3 hr and added to diluted 50 ml dry ether. The resulting yellow precipitate was filtered, washed with dry ether and dried in vacuo at 80° C. for 24 hr, 0.48 g (90%), mp >300° C. Anal. Calculated for C$_{29}$H$_{26}$N$_4$O$_2$.2HCl: C, 65.04; H, 5.27; N, 10.46. Found C, 64.83; H, 4.99; N, 10.22. IR (KBr) 3422, 3235, 2964, 2775, 1609, 1506, 1370, 1289, 1206, 848, 667 cm$^{-1}$. $^1$H NMR (DMSO-d$_6$/D$_2$O/TSP/60° C.) 7.98–7.86 (m, 8H), 7.19 (d, 2H, J=8.79), 7.09 (s, 1H), 7.03 (d, 2H, J=8.3), 3.88 (s, 4H), 3.76 (s, 4H), 2.24 (s, 3H). $^{13}$C NMR (DMSO-d$_6$/D$_2$O/TSP/60° C.) 165.3, 165.3, 154.7, 151.2, 145.7, 139.5, 134.3, 134.2, 135.1, 131.2, 129.6, 129.5, 124.8, 124.1, 123.3, 121.6, 117.7, 106.0, 45.8, 45.6, 20.7.

EXAMPLE 10

Preparation of 2,5-Bis[4-(2-tetrahydropyrimidinyl)phenyl] 3-(4-tolyoxy)furan

A stirred mixture of imidate ester (1.08 g, 0.002 mole) and freshly distilled 1,3-diaminopropane (0.43 g, 0.006 mole) in 30 mL absolute ethanol was gently heated under reflux (protected from moisture) for 12 hr. The excess ethanol was removed under reduced pressure and the residue titrated with 50 mL distilled water. The mixture was made basic with 1M NaOH (pH 10) while cooling and stirring; the precipitated free base was filtered, washed with water, dried and recrystallized from hot ethanol to yield 0.80 g (81.6%); mp 190°-191° C. IR (KBr): 3267, 2931, 2858, 1609, 1505, 1369, 1216, 846, 666 cm$^{-1}$. $^1$H NMR (DMSO-d$_6$/50° C.) 7.88–7.78 (m, 8H), 7.2 (d, 2H, J=8.8), 7.12 (s, 1H), 7.07 (d, 2H, J=8.8), 3.38 (t, 8H, J=5.1), 2.28 (s, 3H), 1.75 (tt, 4H, J=5.1); $^{13}$C NMR (DMSO-d$_6$/50° C.) 154.4, 153.8, 153.4, 150.5, 142.8, 139.0, 134.5, 132.9, 132.4, 130.6, 130.3, 130.3, 126.8, 126.7, 123.1, 122.5, 116.6, 104.1, 41.0, 40.8, 20.0, 19.8; MS m/e 490 (M+).

A suspension of 0.5 g (0.001 mole) of the free base in 5 mL absolute ethanol was treated with 10 mL ethanolic HCl and heated under gentle reflux for 2 hr. 50 mL of dry ether was added and the yellow precipitate thus obtained was filtered and washed with dry ether and dried in vacuo at 60° C. for 12 hr. The yield of yellow solid 0.46 g (82%). Mp >320° C. IR (KBr): 3423, 3117, 3002, 1638, 1609, 1507, 1375, 1315, 1202, 846, 669 cm$^{-1}$; $^1$NMR (DMSO-d$_6$/D$_2$O/TSP/65° C.) 8.12 (d, 2H, J=7.8), 8.08 (d, 2H, J=7.3), 7.88 (d, 4H, J=8.3), 7.32 (d, 2H, J=8.3), 7.22 (s, 1H), 7.16 (d, 2H, J=8.3), 3.6 (br m, 8H), 2.37 (s, 3H), 2.1 (br m, 4H). $^{13}$C NMR (DMSO-d$_6$/D$_2$O/TSP/65° C.): 159.5, 154.8, 151.1, 145.1, 140.9, 139.6, 134.1, 133.9, 133.5, 133.2, 128.7, 128.5, 127.2, 124.8, 117.6, 105.9, 41.5, 41.4, 20.6, 18.2. Anal. calculated for: C$_{31}$H$_{30}$N$_4$O$_2$.2HCl. C, 66.06; H, 5.36; N, 9.94. Found: C, 65.91; H, 5.21; N, 9.88.

EXAMPLE 11

Preparation of 2,5-Bis[4-(2-imidazolinyl)phenyl]-3-methoxy-furan 1,2-Bis(4-bromobenzoyl)-1-methoxyethane. To a solution of 1,2-dibromo-1,2-di(4-bromobenzoyl)ethane (11.1 g, 0.02 mole) in 150 mL dry methanol was added a solution of sodium methoxide in methanol (0.92 g sodium in 50 mL methanol). The yellow brown mixture was refluxed for 1–1.5 hr. The solvent was removed by distillation, the residue was suspended in water and the mixture was extracted with 100 mL chloroform. The chloroform extract was washed with water, dried (Na$_2$SO$_4$) and concentrated. The residue obtained was titrated with dry methanol-ether (3:1) to yield off-white crystalline solid, 6.6 g (78%), mp 153°–154° C. IR (KBr): 3106, 3062, 2932, 1689, 1649, 1583, 1556, 1403, 1223, 1202, 1182, 1086, 1010, 1000, 857, 814, 738, 618, 472 cm$^{-1}$. $^1$H (DMSO-d$_6$/40° C.): 7.95 (d, 2H, J=7.8), 7.77 (4H, J=8.8), 7.72 (d, 2H, J=7.8), 6.89 (s, 1H), 4.03 (s, 3H). $^{13}$C (DMSO-d$_6$/40° C.): 189.9, 187.2, 168.8, 139.9, 135.9, 133.1, 132.2, 131.8, 130.3, 128.1, 127.4, 98.6, 58.5. MS m/e 424 (M+).

2,5-Bis-[4-bromophenyl]-3-methoxy-furan. The methoxyethane prepared above was dissolved in 5 mL PCl$_3$ and heated at reflux for 3 hr. The excess PCl$_3$ was removed by distillation. When treated with ice and water, the residue formed a gummy mass. The mixture was extracted with chloroform, and the organic layer was washed with water, dried (Na$_2$SO$_4$) and purified by column chromatography over silica gel using hexane: ether (4:1 to 2:1). An off-white solid in 62% yield was obtained; mp 112°–113° C. [lit. mp 113° C.; R. E. Lutz, J. Am. Chem. Soc. 51, 3008 (1929)]. IR (KBr) 3062, 2908, 2877, 1617, 490, 1391, 1211, 1160, 1099, 1073, 1034, 1006, 925, 827, 787. $^1$H NMR (CDC$_{13}$) 7.69 (d, 2H, J=8.8), 7.67.5 (m, 4H), 7.47 (d, 2H, J=8.8), 6.64 (s, 1H), 3.9 (s, 3H). $^{13}$C NMR (CDCl$_3$) 149.7, 147.5, 135.5, 131.9, 131.5, 129.4, 129.3, 125.0, 124.5, 121.5, 119.3, 98.6, 58.6. MS m/e 408 (M+).

2,5-Bis(4-cyanophenyl)-3-methoxyfuran. A mixture of 2,5-bis(bromophenyl)-3-methoxyfuran (4.08 g, 0.01 mole) and cuprous cyanide (3.09 g, 0.035 mole) in 10 mL dry N-methyl-2-pyrrolidone was heated ca. 200° C. under N$_2$ for 2.5 hr. The mixture was cooled and poured into 200 mL of water and the precipitated yellow-brown solid was filtered and washed thoroughly with water. The solid was resuspended in water (50 mL) and 100 mL of 10% NaCN and stirred for 2 hr. The slurry was filtered, washed with water, dried and suspended in 250 mL of acetone and passed through a neutral alumina column. On elution with acetone a yellow solid resulted. On recrystallization from CHCl$_3$:ether (1:1) it gave (1.8 g, 60%) mp 257°–258° C. IR (KBr) 3128, 2223, 1608, 1599, 1501, 1409, 1174, 1163, 1027, 924, 836, 815, 651, 537 cm$^{-1}$. $^1$H NMR (DMSO/45° C.) 8.03 (d, 2H, J=8.3), 7.95 (d, 2H, J=8.79), 7.91 (d, 2H, J=8.3), 7.85 (d, 2H, J=8.79), 7.62 (s, 1H), 4.0 (s, 3H). $^{13}$C NMR (DMSO/45° C.) 150.0, 149.8, 134.6, 133.4, 133.2, 132.7, 132.5, 124.0, 122.7, 118.9, 118.5, 110.0, 107.6, 102.4, 59.0. MS m/e 300 (M+). Anal. Calculated for: C$_{19}$H$_{12}$N$_2$O (300.31): C, 75.98; M, 4.03; N, 9.33; Found: C, 76.02; H, 4.04; N, 9.36.

2,5-Bis[4-(2-imidazolinyl)phenyl]-3-methoxy-furan. The bis-nitrile prepared above (0.9 g, 0.003 mole) was suspended in 70 mL dry ethanol, saturated with dry HCl gas at 0°–5° C. and stirred under dry conditions for 3–4 days. The mixture was diluted with 200 mL dry ether and the yellow amidate ester was filtered and washed with dry ether and the solid was dried in vacuo for 5–6 hr to yield 1.2 g (86%). The solid was resuspended in 30 mL dry ethanol and refluxed gently with 0.46 g (0.008 mole) dry ethylenediamine for 12 hr. The solvent was removed by distillation. The residue was suspended with 50 mL cold water and made basic with 1M NaOH. The yellow precipitate was filtered, washed with water and dried. Recrystallization from ethanol-ether mixture yielded 0.74 g (75%) mp 186°–187° C (dec.). IR (KBr) 3444, 3245, 2931, 2857, 1601, 1512, 1397, 1366, 1277, 1162, 1104, 1031, 926, 842, 743, 670 cm$^{-1}$. $^1$H (DMSO-d$_6$/60° C.) 7.93–7.86 (m, 8H), 7.32 (s, 1H), 3.98 (s, 3H), 3.69 (s, 4H), 3.67 (s, 4H). $^{13}$C NMR (DMSO-d$_6$/60° C.: 163.3, 163.1, 150.0, 148.6, 138.3, 134.7, 131.9, 131.3, 128.9, 127.6, 126.1, 123.0, 121.9, 100.6, 58.7, 49.0, 48.5. MS m/e 386 (M+).

The free base 0.58 g (0.0015 mole) was dissolved in 10 mL hot ethanol and treated with 10 mL sat. ethanolic HCl. The mixture was heated at reflux for 30 min. The volume was reduced under vacuum to 5–6 mL. The resulting mixture was diluted to 60 mL of dry ether. The yellow crystalline solid obtained was filtered, washed with dry ether and dried in vacuo at 60° C. for 12 to yield 0.62 g (83%), mp 189°–190° C. (dec.). IR (KBr): 3422, 3128, 2975, 1599, 1510, 1405, 1363, 1285, 1207, 1028, 845, 666 cm$^{-1}$. $^1$H (D$_2$O/TSP/50° C.) 7.52–7.43 (m, 8H), 6.87 (s, 1H), 3.92 (s, 3H), 3.86 (s, 8H). $^{13}$C (D$_2$O/TSP/50° C.) 167.2, 153.1, 152.4, 137.6, 137.6, 137.2, 130.9, 130.7, 126.5, 125.4, 122.1, 119.8, 104.2, 61.5, 47.0, 46.9. Anal. Calculated for: C$_{23}$H$_{22}$N$_4$O$_2$-0.5 H$_2$O-2HCl: C, 58.97; H, 5.38; N, 11.96. Found: C, 59.16; H, 5.35; N, 11.80.

EXAMPLE 12

Preparation of 2,5-Bis[4(N-cyclo-propylguanyl)phenyl furan

A mixture of the imidate ester (1.3 g, 0.003 mole), cyclopropylamino (0.43 g, 0.0075 mole) in 35 mL of dry ethanol was stirred overnight. The solvent was removed in vacuo and water was added to make a yellow solution. The solution was made basic with 1M NaOH while cooling and stirring. The solid which formed was filtered, washed with water and dried. The solid was dissolved in chloroform, dried over Na$_2$SO$_4$ and the solvent removed. The residue was recrystallized from ether:CHCl$_3$ (5:1) to give a pale yellow solid 0.8 g (709%) mp 185°–186° C. (dec.). IR (KBr): 3464, 3320, 3080, 1610, 1510, 1364, 1022, 848, 791 cm$^{-1}$. $^1$H NMR (CDC$_{13}$): 7.71 (br s, 8H), 6.78 (s, 2H), 5.3 (v br, 4H), 2.6 (br m, 2H), 0.87–0.81 (m, 4H), 0.67–0.62 (m, 4H). $^{13}$C NRM (CDC$_{13}$+DMSO-d$_6$): 159.6, 152.2, 134.8, 130.7, 126.4, 122.6, 107.7, 25.7, 6.04. MS m/e 388 (M+).

The free base (0.6 g, 0.0015 mole) was suspended in 3 mL of dry ethanol and was treated with 6 mL ethanolic HCl and heated gently at 65° C. for 1 hr. The yellow solution was diluted with 50 mL dry ether and filtered, washed with dry ether and dried in vacuo at 75° C. for 12 hr. The yield of yellow solid was 0.55 g (80%), mp >310° C. (dec.). IR (KBr): 3369, 3181, 3037, 1665, 1607, 1502, 1032, 782, 674 cm$^{-1}$. $^1$H NMR (DMSO-d$_6$): 10.24 (s, 2H), 9.86 (s, 2H), 9.27 (s, 2H), 8.06 (d, 4H, J=7.94), 7.95 (d, 4H, J=8.54), 7.42 (s, 2H), 2.87 (br m, 2H), 1.09–0.85 (m, 8H). $^{13}$C NMR (DMSO-d$_6$): 163.9, 152.3, 133.7, 129.1, 126.6, 123.5, 111.3, 24.7, 6.5. Anal. Calculated for: C$_{24}$H$_{24}$N$_4$O-2HCl: Cal. C, 63.02; H, 5.73; N, 12.25. Found: C, 62.89; H, 5.95; N, 12.00.

EXAMPLE 13

Preparation of Sample for Fluorescent Detection

Chemicals. DAPI, Hoechst 33258, and distamycin were obtained from Sigma Chemical Co.

Sources of samples. *Giardia lamblia* were cultured by standard methods as previously described (C. A. Bell, et al., Agents and Chemother. 37, 2668–2673 (1993)), released from the culture tubes by chilling, and washed with HBSS$^-$ (Hanks Balanced Salt Solution, available from Sigma Chemical Co.) buffer. The organisms were then incubated with the dye for five minutes and washed once with HBSS$^-$ buffer before mounting for microscopy. Metaphase chromosome spreads were prepared from human lymphocytes by standard methods. Staining by all of the dyes followed standard protocols used for DA (distamycin)/DAPI staining of C bands (O. Miller, Principles and Practices in Medical Genetics (Longman Group Limited, New York 1983) and D. Silvonen, ACT Cytogenetic Lab Manual (University of California, San Francisco (1980)).

Specifically, when staining with DAPI, the slide was soaked in a buffer solution, MacIlvaine's buffer (pH 7.5), for about 10 minutes (MacIlvaine's buffer was prepared as known by mixing an anhydrous citric acid solution (0.2M, 19.2 g/liter) and an anhydrous sodium phosphate dibasic ($Na_2HPO_4$) solution (0.2M, 28.4 g/liter)). The slide was stained using DAPI (0.2 µg/ml) for about 10 minutes and rinsed with MacIlvaine's buffer. This same staining procedure was followed for staining with the compounds of Formula (I), except that the slide was stained using 0.02 µg/ml of the compound.

EXAMPLE 14

Nucleic Acid Detection

Tissues were mounted in either HBSS⁻ buffer or glycerol on a slide and covered with a glass coverslip. Special materials were not needed. The samples were viewed under a Nikon photomicroscope equipped with UV optics (filters with excitation of 360 nm and emission of 460 nm) and neofluor lenses. The images were photographed with either Ektachrome 1600 ASA film or Technical Pan 400 ASA black and white film. Exposure times were 0.1 to 5 seconds.

The photographs show a comparison of nuclear staining of G. lamblia by the dyes of Formula (I) in comparison to DAPI and Hoechst 33258. The highly DNA-specific dye, 2,5-bis[4-(4,5,6,7-tetrahydro-1H-1,3-diazepin-2-yl)phenyl]furan, had no background staining of the giardial cytoplasm, indicating that no binding to RNA or to cytoskeleton elements occurs. For DAPI, Hoechst 33258, and 2,5-bis(4-amidinophenyl)furan, significant staining of the giardial cytoplasm was observed. For DAPI and 2,5-bis(4-amidinophenyl)furan, there was apparent staining of microtubular or filamentous structures as well. It has been reported that DAPI can stain tubulin and microtubules (D. Bonne, et al., J. Biol. Chem. 260, 2819–2825 (1985)), but the authors reported that this staining could not be observed in intact fibroblasts. These photographs suggest that in giardia, DAPI stains a structural element that could be tubulin as well as the intense staining of nucleic acids.

In addition to giardia, human metaphase chromosomes stained with the compounds of Formula (I) were examined in comparison to DAPI since it is widely used to examine markers of AT-rich regions of chromosomes that produce the "C bands" on chromosomes 1,9,15,16, and Y (O. Miller, Principles and Practices in Medical Genetics (Longman Group Limited, New York 1983)). The furan dyes 2,5-bis[4-(4,5,6,7-tetrahydro-1H-1,3-diazepin-2-yl)phenyl]furan; 2,5-bis{[4-(N-isopropyl)amidino]phenyl}furan; and 2,5-bis(4-amidinophenyl)furan produced substantially similar staining patterns to that of DAPI. The furan dyes emit a blue color of slightly different wavelength than that emitted by DAPI. This can result in less light scatter than that observed with DAPI, and thus there is the potential to delineate more detail. In addition, special handing and/or storage protocols are not needed with the furan dyes.

The dicationic furans have been also examined in many other types of tissue such as bacteria, yeast, plants, and tissue culture cells. In each case, their DNA detection sensitivity is comparable to that of DAPI with the advantage that their deeper blue color and DNA specificity properties can elucidate more detail.

EXAMPLE 15

Nucleic Acid Binding Measurements

The binding affinities for the dyes to nucleic acids have been previously described (W. D. Wilson, et al., Biochemistry 3, 4098–4104 (1993); W. D. Wilson, et al., Molecular Basis of Specificity in Nucleic Acid-Drug Interactions (Kluwer Academic Publishers, Amsterdam 1990), pp. 331–353) except for the compounds of Formula (Ia) and (Ib). The nucleic acid binding parameters were determined for these compounds in the same manner as the others. Specifically, nucleic acid binding parameters were determined using thermal melting (Tm) studies using a Cary 219 spectrophotometer interfaced to an Apple IIe microcomputer. The temperature of the Cary was controlled by a Haake PG20 temperature programmer connected to a Haake A81 refrigerated bath which was set to raise the temperature by 0.5° C. per minute. A thermistor fixed into a reference curvette was used to monitor the temperature. Tm comparisons were conducted with the RNA polymer poly(A).poly (U) and the corresponding sequence DNA poly(dA).poly (dT). The polymers were added to 1 mL of buffer in 1 cm path length reduced volume quartz cells, and the concentration determined by measuring the absorbance at 260 nm. Experiments were generally conducted at a $5\times10^{-5}$M concentration of DNA base pairs and a ratio of compound/base pair of 0.6. Compounds were compared by the increase in Tm ($\Delta Tm$=Tm of the complex–Tm of the free nucleic acid) they produced.

Table I compares the DNA and RNA affinities of the fluorescent dyes 2,5-bis(4-amidinophenyl)furan (DB75); 2,5-bis[4-(4,5,6,7-tetrahydro-1H-1,3-diazepin-2-yl)phenyl]furan (DB161); 2,5-bis{[4-(N-isopropyl)amidino]phenyl}furan (DB181); and 2,5-bis[4-(1,4,5,6-tetrahydropyrimidin-2-yl)phenyl]furan (DB103), in comparison to the compounds DAPI and Hoechst 33258.

TABLE I

Structures of the Dyes and Their Nucleic Acid Binding as Determined from Melting Temperatures

| Structure | ΔTm(A-U) | ΔTm(dA-dT) |
| --- | --- | --- |
| DAPI | 3.9 | >25 |
| Hoechst 33258 | 17.5 | >25 |
| DB75 | 5.7 | 24.6 |
| DB103 | 2.5 | >25 |
| DB161 | 0 | >26 |
| DB181 | 1.5 | >26 |

EXAMPLE 16

Spectral Measurements

The dyes either with or without DNA or RNA present were scanned for with absorption maxima in a Shimadzu double-beam spectrophotometer. The determination of their fluorescent excitation and emission maxima were determined on an LKB fluorimeter. The absorbance maxima, excitation coefficients, excitation maxima, and emission maxima are shown in Table II below.

TABLE II

| Compound | Absorbance (nm) | Fluorescence Excitation max (nm) | Fluorescence Emmision max (nm) | R1 | R2 | R3 | R4 | R5 |
|---|---|---|---|---|---|---|---|---|
| DB75 | 355 | 359 | 462 | H | H | H | H | H |
| DB60 | 365 | 366 | 459 | —(CH$_2$)$_2$— | | H | H | H |
| DB103 | 355 | 356 | 445 | —(CH$_2$)$_3$— | | H | H | H |
| DB99 | 365 | 363 | 468 | H | H | H | CH$_3$ | CH$_3$ |
| DB116 | 388 | 394 | 503 | —(CH$_2$)$_2$— | | H | H | OCH$_3$ |
| DB154 | 375 | 381 | 495 | —(CH$_2$)$_2$— | | H | H | O-Phenyl-CH$_3$ |
| DB155 | 354 | 354 | 471 | —(CH$_2$)$_3$— | | H | H | O-Phenyl-CH$_3$ |
| DB159 | 387 | 390 | 510 | aminoethylamidobenzimidazole | | | H | H |
| DB160 | 375 | 385 | 467 | hexahydrobenzimidazole | | | H | H |
| DB161 | 354 | 354 | 470 | —(CH$_2$)$_4$— | | H | H | H |
| DB180 | 356 | 356 | 469 | —(CH$_2$)$_2$— | | —(CH$_2$)$_2$OH | H | H |
| DB181 | 354 | 356 | 454 | H | H | —CH(CH$_3$)$_2$ | H | H |
| DB182 | 357 | 356 | 458 | H | H | —(CH$_2$)$_3$N(CH$_3$)$_2$ | H | H |

EXAMPLE 17

Cytoskeletal Element Detection

Samples were prepared and viewed as described above in Examples 9 and 10, except that the samples were stained using the following compounds: DB 99, DB 154, and DB 155. The photographs show that for the compounds DB 99, DB 154 and DB 155, staining for cytoskeleton elements, i.e., of microtubular or filamentous structures of *G. lamblia*, occurs.

For the following examples (Examples 18–26), melting points were recorded using a Thomas Hoover (Uni-Melt) capillary melting point apparatus and are uncorrected. $^1$H NMR and $^{13}$C NMR spectra were recorded employing a Varian GX400 spectrometer and chemical shifts(d) are in ppm relative to TMS unless otherwise noted. Mass spectra were recorded on a VG Instruments 70-SE spectrometer (Georgia Institute of Technology, Atlanta, Ga.). IR spectra were recorded using a Michelson 100 (Bomem, Inc.) instrument. Elemental analysis were obtained from Atlantic Microlab Inc. (Norcross, Ga.) and are within +0.4 of the theoretical values. All chemicals and solvents were purchased from Aldrich Chemical Co. or Fisher Scientific.

EXAMPLE 18

Preparation of 2,5-Bis(5-amidino-2-benzimidazolyl)pyrrole 2,5-Bis(5-amidino-2-benzimidazolyl)pyrrole (DB 192). A solution of pyrrole-2,5-dicarboxaldehyde (Cresp, T., Sargent, M., *J. Chem. Soc.* Perkin Trans. 1, 2961 (1973)) (0.25 g, 2 mmol), 3,4-diaminobenzamidine (Fairley T.A.A. Tidwell R. R., Donkor I, Naiman N. A., Ohemeng K. A., Bentley A. and Cory M. J., *Med. Chem.* 36, 1746 (1993)) (0.6 g, 4 mmol) and 1,4-benzoquinone (0.432 g, 4 mmol) in ethanol (40 ml) was heated at reflux for 4 hours (under nitrogen) (Kumar, S., Konsal, V., Bhaduri, A., *Indian J. Chem.* 20B, 254 (1981). The reaction mixture was cooled to room temperature and the dark solid was collected by filtration, washed with cold ethanol, anhydrous ether and dried to yield 0.45 g (59%) of the free base. This solid was dissolved slowly in hot ethanol (300 ml) and filtered. The filtrate volume was reduced to 70 ml and acidified with HCl-saturated ethanol. After standing overnight in the refrigerator, the green solid was collected by filtration, washed with anhydrous ether and dried under vacuum to yield 0.5 g (76%) yield of solid. mp >300° C. $^1$HNMR (DMSO-d$_6$) (7.54 (s, 2H, pyrrole), 7.80 (dd, J=8.8 and 0.8 Hz, Ar—H, 2H), 7.87 (d, J=8.4 Hz, 2H, Ar—H), 8.25 (s, 2H, Ar—H), 9.18, 9.48 (brs, brs, NH). Anal. (C$_{20}$N$_{17}$N$_9$.3HCl.3H$_2$O) C,H,N. MS: m/e 384 (M+1).

EXAMPLE 19

Preparation of 2,5-Bis-[5-(2-imidazolinyl)-2-benzimidazolyl]pyrrole 2,5-Bis-[5-(2-imidazolinyl)-2-benzimidazolyl]pyrrole (DB 201). A protocol similar to that used in Example 18 above was used for the condensation of pyrrole-2,5-dicarboxaldehyde and 2-(3,4-diaminophenyl)imidazoline to give a 86% yield of solid. mp >300° C. $^1$HNMR (DMSO-d$_6$) (4.04 (s, 8H, NCH$_2$CH$_2$N), 7.39 (s, 2H, pyrrole), 7.86 (d, J=8.8 Hz, 2H, Ar—H), 7.92 (dd, J=8.4 and 1.6 Hz, 2H, Ar—H), 8.44 (s, 2H, Ar—H), 10.71 (s, NH). Anal. (C$_{24}$H$_{21}$N$_9$.3HCl.4H$_2$O) C,H,N. MS: m/e 436 (M+1).

EXAMPLE 20

Preparation of 2,6-Bis[5-(2-imidazolinyl)-2-benzimidazolyl]pyridine 2,6-Bis[5-(2-imidazolinyl)-2-benzimidazolyl]pyridine (DB202). A protocol similar to that used in Examples 18 and 19 above was used for condensation of 2,6-pyridine carboxyaldehyde and 2-(3,4-diaminophenyl)imidazoline to give an 85% yield of solid. mp >300° C. $^1$HNMR (DMSO-d$_6$) (4.05 (s, 8H, N—CH$_2$CH$_2$N), 7.96 (m, 4H, Ar—H), 8.30 (t, 1H, pyridine), 8.49–8.51 (m, 4H, Ar—H), 10.71 (s, NH). Anal. (C$_{25}$H$_{21}$N$_9$.3HCl.3H$_2$O) C,H,N. MS: m/e 448 (M+1).

EXAMPLE 21

Preparation of 1-Methyl-2,5-Bis(5-amidino-2-benzimidazolyl)pyrrole

1-Methyl-2,5-Bis(5-amidino-2-benzimidazolyl)pyrrole (DB191). A protocol similar to that described above in Examples 18–20 was employed for the condensation of 3,4-diaminobenzamidine (Fairley T. A., Tidwell R. R., Donkor I., Naiman N. A., Ohemeng K. A., Bentley A. and Cory M. J., *Med. Chem.* 36, 1746 (1993)) with 1-methylpyrrole-2,-5-dicarboxaldehyde to yield 0.48 g (46%) of product. mp >300° C.; $^1$HNMR (DMSO-d$_6$) (4.72 (s, 3H, CH$_3$—N), 7.33 (s, 2H, pyrrole), 7.73 (dd, J=8 and 1.2 Hz, 2H, Ar—H), 7.80 (d, J=8.4 Hz, Ar—H), 8.19 (s, 2H, Ar—H) 9.11, 9.38 (brs, brs, NH-amidine). Anal. (C$_{21}$H$_{19}$N$_9$.3HCl.H$_2$O) C,H,N. MS:m/e 398 (M+1).

EXAMPLE 22

Preparation of 1-methyl-2,5-bis[5-(2-imidazolyl)-2-benzimidazolyl]pyrrole 1-methyl-2,5-bis[5-(2-imidazolyl)-2-benzimidazolyl]pyrrole (DB 206). A protocol similar to that described above in Examples 18–21 was employed for the condensation of 2-(3,4-diaminophenyl)imidazoline with 1-methylpyrrole-2,-5-dicarboxaldehyde. A yield of 83% of solid, mp >300° C., was obtained. $^1$HNMR (4.04 (s, 8H, NCH$_2$CH$_2$N), 4.72 (s, 3H, CH$_3$N), 7.30 (s, 2H, pyrrole), 7.84 (qAB, J=8.4 and 8 Hz, 4H, Ar—H), 8.36 (s, 2H, Ar—H), 10.60 (s, NH). Anal. (C$_{25}$H$_{23}$N$_9$·3HCl·3H$_2$O) C,H,N. MS: m/e 450 (M+1).

EXAMPLE 23

Preparation of 1-Methyl-2,5-bis[5-(1,4,5,6-tetrahydro-2-pyrimidinyl)-2-benzimidazolyl]pyrrole 1-Methyl-2,5-bis[5-(1,4,5,6-tetrahydro-2-pyrimidinyl)-2-benzimidazolyl]pyrrole (no DB number). A protocol similar to that described above for Examples 18–22 was employed for the condensation of 2-(3,4-diaminophenyl)tetrahydropyrimidine with 1-methypyrrole-2,5-dicarboxaldehyde. A yield of 83% of solid, mp >300° C., was obtained. $^1$HNMR (2.01 (m, 4H, CH$_2$), 3.52 (brs, 8H, CH$_2$N), 4.72 (s, 3H, CH$_3$N), 7.31 (s, 2H, pyrrole), 7.60 (d, J=8.4 Hz, 2H, Ar—H), 7.80 (d, J=8.4 Hz, 2H, AR—H), 8.06 (s, 2H, Ar—H), 9.99 (s, NH). Anal. (C$_{27}$H$_{27}$N$_9$·3HCl·4H$_2$O) C,H,N. MS: m/e 478 (M+1).

EXAMPLE 24

Preparation of 2,6-Bis(5-amidino-2-benzimidazolyl)pyridine 2,6-Bis(5-amidino-2-benzimidazoyl)pyridine (DB 205). A protocol similar to that described in Examples 18–23 above was used to condense 2,6-pyridine dicarboxaldehyde with 3,4-diaminobenzamidine to yield 89% of a solid, mp >300° C. $^1$HNMR (DMSO-d$_6$) (7.79 (dd, J=8.4 and 1.6 Hz, 2H, Ar—H), 7.94 (d, J=8.4 Hz, 2H, Ar—H), 8.28–8.34 (m, 3H, Ar—H), pyridine), 8.51 (d, J=8 Hz, 2H, pyridine), 9.12, 9.45 (brs, brs, NH). Anal. (C$_{21}$H$_{17}$N$_9$·3HCl·2H$_2$O) C,H,N. MS: m/e 396 (M+1).

EXAMPLE 25

Preparation of 2,6-Bis[5-(1,4,5,6-tetrahydro-2-pyrimidinyl)-2-benzimidazolyl]pyridine 2,6-Bis[5-(1,4,5,6-tetrahydro-2-pyrimidinyl)-2-benzimidazolyl]pyridine (DB 218). A protocol similar to that described above in Examples 18–24 was used to condense 2,6-pyridine dicarboxaldehyde with 2-(3,4-diaminophenyl)tetrahydropyrimidine to give an 89% yield of solid, mp >300° C. $^1$HNMR (DMSO-d$_6$) (2.03 (m, 4H, CH$_2$), 3.54 (brs, 8H, CH$_2$N), 7.66 (d, J=8.4 Hz, 2H, Ar—H), 7.84 (d, J=8.4 Hz, 2H, Ar—H), 8.17 (s, 2H, Ar—H), 8.29 (t, 1H, pyridine), 8.43 (d, J=8 Hz, 2H, pyridine), 10.04 (s, NH). Anal. C$_{27}$H$_{25}$N$_9$·3HCl·4H$_2$O C,H,N. MS: m/e 476 (M+1).

EXAMPLE 26

Preparation of 2,5-Bis(5-amidino-2-benzimidazolyl)furan 2,5-Bis(5-amidino-2-benzimidazolyl]furan. A protocol similar to that described above in Examples 18–25 above was used to condense 2,5-furan dicarboxyaldehyde with 3,4-diaminobenzamidine. A solution of 2,5-furan dicarboxyaldehyde (0.25 g, 2 mmol), 3,4-diaminobenzamidine (0.6 g, 4 mmol) and benzoquinone (0.43 g, 4 mmol) in ethanol (100 mL) was refluxed under nitrogen for 4 hours. After cooling, solvent was reduced and to the residue dry ether was added. The precipitated solid was filtered and washed with dry ether. The yellow-green solid was acidified with concentrated HCl. After standing overnight ether was added and the solid was collected by filtration, washed with dry ether, and dried in vacuum at 90° C. for 48 hours. Yield 0.5 g (52.2%) of the yellow-green powder, mp >300° C. MS (FAB): m/z 385 (M$^+$+1); HRMS: calc. mass (free base): 385.1525 (M$^+$+1); observed mass: 385.1535, $^1$H NMR (DMSO-d$_6$, TMS) δ: 9.30 s, 4H (N—H); 8.95 s, 4H (N—H); 8.19 s, 2H (phenyl); 7.81 d, 2H, J=8.8 Hz; 7.72 d, 2H, J=8.4 Hz; 7.60 s 2H (furan), $^{13}$C NMR (DMSO-d$_6$+D$_2$O) δ:166.8; 146.3; 146.1; 142.2; 139.7; 123.4; 122.7; 117.1; 116.1; 115.4. Anal. (C$_{20}$H$_{16}$N$_8$O·2HCl·1.5H$_2$O) C,H,N

EXAMPLE 27

Preparation of 2,5-Bis[5-(1-imidazolinyl)-2-benzimidazolyl]furan 2,5-Bis[5-(2-imidazolinyl)-2-benzimidazolyl]furan. A protocol similar to that described above in Examples 18–26 above was used to condense 2,5-furan dicarboxyaldehyde with 2-(3,4-diaminophenyl)imidazoline. A solution of 2,5-furan dicarboxyaldehyde (0.25 g, 2 mmol), 2-(3,4-diaminophenyl)imidazoline (0.7 g, 4 mmol) and benzoquinone (0.43 g, 4 mmol) in ethanol (100 mL) was refluxed under nitrogen for 4 hours. After cooling, solvent was reduced and to the residue dry ether was added. The precipitated solid was filtered and washed with dry ether. The yellow-green solid was acidified with concentrated HCl. After standing overnight ether was added and solid was collected by filtration, washed with dry ether, and dried in vacuum at 90° C. for 3 days. Yield 0.45 g (38.1%) of the green powder, mp >300° C. MS (FAB): m/z 437 (M$^+$+1); HRMS: calc. mass (free base): 437.1838 (M$^+$+1); observed mass: 437.1832, $^1$H NMR (DMSO-d$_6$, TMS) δ: 10.53 s, 4H (N—H); 8.38 s, 2H; 7.87 d, 2H, J=8.5 Hz; 7.83 d, 2H, J=8.2 Hz; 7.62 s, 2H; 4.04 s, 8H. $^{13}$C NMR (DMSO-d$_6$+D$_2$O, TMS): δ166.3; 146.2; 146.1; 142.3; 139.8; 123.7; 117.6; 116.9; 116.1; 115.5; 45.0. Anal. (C$_{24}$H$_{20}$N$_8$O·2HCl·5H$_2$O) C, H, N

EXAMPLE 28

Preparation of 2,5-Bis(5-N-isopropylamidino-2-benzimidazolyl)furan 2,5-Bis(5-N-isopropylamidino-2-benzimidazolyl]furan. A protocol similar to that described above in Examples 18–27 above was used to condense 2,5-furan dicarboxyaldehyde with 3,4-diamino-N-isopropylbenzamidine. A solution of 2,5-furan dicarboxyaldehyde (0.25, 2 mmol), 3,4-diamino-N-isopropylbenzamidine (0.77 g, 4 mmol), and benzoquinone (0.43 g, 4 mmol) in ethanol (100 mL) was refluxed under nitrogen for 4 hours. After cooling, solvent was reduced and to the residue dry ether was added. The precipitated solid was filtered and washed with dry ether and dried. After drying the green solid was dissolved in anhydrous ethanol saturated with HCl (50 mL) and heated until boiling started, then allowed to cool. The green solid was collected by filtration, and dried in vacuum at 90° C. for 3 days. Yield 0.67 g (53.6%) of the yellow-green powder, mp >300° C. MS (FAB): m/z 469 (M⁺+1); HRMS: calc. mass (free base): 469.2464 (M⁺+1); observed mass: 469.2475. $^1$H NMR (DMSO-d$_6$, TMS): δ9.60+9.58 s+s, 2H (N—H); 9.45 s, 2H (N—H); 9.45 s 2H (N—H); 9.04 s, 2H (N—H); 8.06 s, 2H (phenyl); 7.82 d, 2H, J=8.4 Hz; 7.69 s, 2H (furan); 7.62 d, 2H, J=8.2 Hz; 4.09 m, 2H (CH), J=7.02 Hz; 1.32 d 12H (CH$_3$), J=6.3 Hz; $^{13}$C NMR (DMSO-d$_6$+D$_2$O, TMS): δ162.8; 145.9; 145.1; 140.9; 138.5; 124.5; 124.0; 116.9; 115.9; 115.9; 45.9; 21.7. Anal. (C$_{26}$H$_{28}$N$_8$O.3HCl.5H$_2$O) C,H,N

EXAMPLE 29

Spectral Measurements

The dyes either with or without DNA or RNA present were scanned for with absorption maxima in a Shimadzu double-beam spectrophotometer. The determination of their fluorescent excitation and emission maxima were determined on an LKB fluorimeter. The absorbance maxima, excitation coefficients, excitation maxima, and emission maxima are shown in Table III below.

TABLE III

Biophysical Data

| Compound | Aborbance Max (nm) | Fluorescence Excitation max (nm) | Emission max (nm) | PHOTO COMMENTS |
|---|---|---|---|---|
| DB191 | 354, 218 | 230, 354 | 468, 472 | blue, good, broad peak |
| DB206 | 359, 230 | 355 | 454 | |
| DB192 | 359, 225 | 358, 230 | 355, 460 | |
| DB201 | 366, 235 | 235, 366 | 466, 469 | broad peak, good, nuclear specific |
| DB205 | 325, 250, 218 | 325, 250 | 374, 377 | |
| DB202 | 329, 250 | 329 | 420 | quenches, stains all over |
| DB218 | 325, 249 | 325 | 377 | |

The foregoing examples are illustrative of the present invention, and are not to be construed as limiting thereof. The invention is defined by the following claims, with equivalents of the claims to be included therein.

That which is claimed is:

1. A method for the fluorescent detection of a nucleic acid comprising:

(a) contacting said nucleic acid with a compound according to Formula (II)

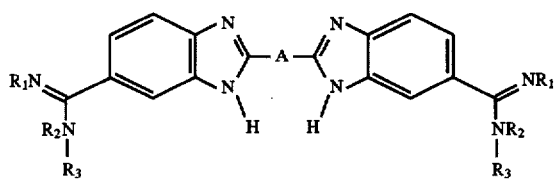

(II)

wherein:

R$_1$ and R$_2$ are each independently selected from the group consisting of H, lower alkyl, alkoxyalkyl, cycloalkyl, aryl, alkylaryl, hydroxyalkyl, aminoalkyl, or alkylaminoalkyl, or R$_1$ and R$_2$ together represent a C$_2$ to C$_{10}$ alkyl, hydroxyalkyl, or alkylene or R$_1$ and R$_2$ together are:

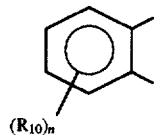

wherein n is from 1 to 3 and R$_{10}$ is H or —CONHR$_{11}$NR$_{15}$R$_{16}$, wherein R$_{11}$ is lower alkyl, and R$_{15}$ and R$_{16}$ are each independently selected from the group consisting of H and lower alkyl;

R$_3$ is H, hydroxy, lower alkyl, cycloalkyl, aryl, alkylaryl, alkoxyalkyl, hydroxycycloalkyl, alkoxycycloalkoxy, hydroxyalkyl, aminoalkyl or alkylaminoalkyl;

A is a heterocyclic aromatic group selected from the group consisting of:

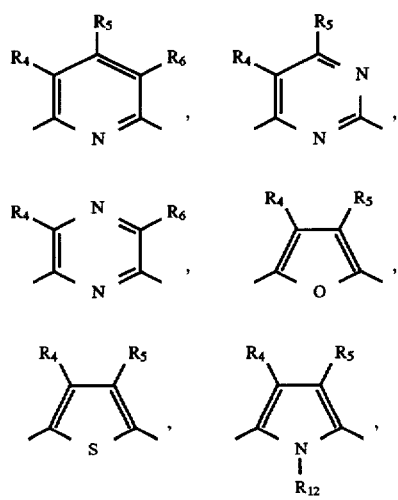

-continued

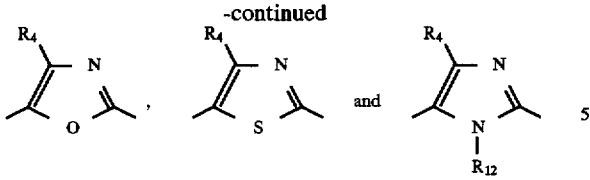

wherein $R_4$, $R_5$, and $R_6$ are each independently selected from the group consisting of H, lower alkyl, halogen, aryl, arylalkyl, aminoalkyl, aminoaryl, oxyalkyl, oxyaryl, or oxyarylalkyl;

$R_{12}$ is hydrogen, lower alkyl, hydroxy, aminoalkyl or alkylaminoalkyl, or a physiologically acceptable salt thereof; and (b) exposing said nucleic acid to light to induce fluorescence of said compound of Formula (II); and (c) thereby detecting said nucleic acid.

2. A method according to claim 1 wherein said nucleic acid is DNA.

3. A method according to claim 1 wherein said nucleic acid is RNA.

4. A method according to claim 1, wherein A has the structural formula

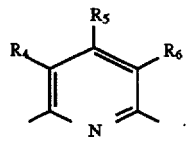

5. A method according to claim 1, wherein A has the structural formula

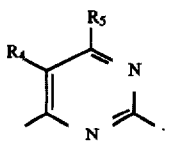

6. A method according to claim 1, wherein A has the structural formula

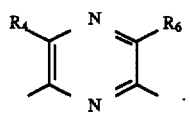

7. A method according to claim 1, wherein A has the structural formula

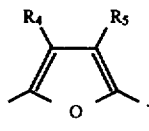

8. A method according to claim 1, wherein A has the structural formula

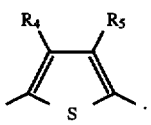

9. A method according to claim 1, wherein A has the structural formula

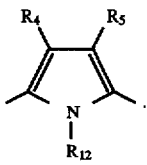

10. A method according to claim 1, wherein A has the structural formula

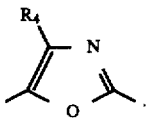

11. A method according to claim 1, wherein A has the structural formula:

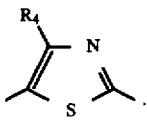

12. A method according to claim 1, wherein A has the structural formula

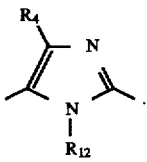

13. A method according to claim 1, wherein and $R_2$ together represent a $C_2$ to $C_4$ alkylene, and $R_3$ is H.

14. A method according to claim 13, wherein $R_1$ and $R_2$ together represent

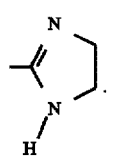

15. A method according to claim 13, wherein $R_1$ and $R_2$ together represent

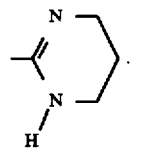

16. A method according to claim 1, wherein each of $R_1$, $R_2$ and $R_3$ is H.

17. A method according to claim 1, wherein each of $R_1$ and $R_3$ is H and $R_2$ is lower alkyl.

18. A method according to claim 1, wherein said compound is selected from the group consisting of:
2,5-bis(5-amidino-2-benzimidazolyl)pyrrole;
2,5-bis-[5-(2-imidazolinyl)-2-benzimidazolyl]pyrrole;
2,6-bis[5-(2-imidazolinyl)-2-benzimidazolyl]pyridine;
1-methyl-2,5-bis(5-amidino-2-benzimidazolyl)pyrrole;
1-methyl-2,5-bis[5-(2-imidazolyl)-2-benzimidazolyl]pyrrole;
1-methyl-2,5-bis[5-(1,4,5,6-tetrahydro-2-pyrimidinyl)-2-benzimidazolyl]pyrrole;
2,6-bis(5-amidino-2-benzimidazolyl)pyridine;
2,6-bis[5-(1,4,5,6-tetrahydro-2-pyrimidinyl)-2-benzimidazolyl]pyridine;
2,5-bis(5-amidino-2-benzimidazolyl)furan;
2,5-bis[5-(2-imidazolinyl)-2-benzimidazolyl]furan;
2,5-bis(5-N-isopropylamidino-2-benzimidazolyl)furan;
and the physiologically acceptable salts thereof.

19. A method for the selective fluorescent detection of DNA in a nucleic acid mixture containing DNA and RNA, said method comprising:

(a) contacting said nucleic acid mixture with a compound according to Formula (II)

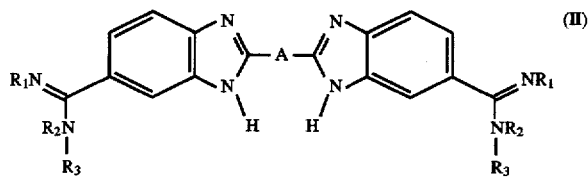

wherein:

$R_1$ and $R_2$ are each independently selected from the group consisting of H, lower alkyl, alkoxyalkyl, cycloalkyl, aryl, alkylaryl, hydroxyalkyl, aminoalkyl, or alkylaminoalkyl, or $R_1$ and $R_2$ together represent a $C_2$ to $C_{10}$ alkyl, hydroxyalkyl, or alkylene or $R_1$ and $R_2$ together are:

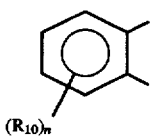

wherein n is from 1 to 3 and $R_{10}$ is H or —$CONHR_{11}NR_{15}R_{16}$, where $R_{11}$ is lower alkyl and $R_{15}$ and $R_{16}$ are each independently selected from the group consisting of H and lower alkyl;

$R_3$ is H, hydroxy, lower alkyl, cycloalkyl, aryl, alkylaryl, alkoxyalkyl, hydroxycycloalkyl, alkoxycycloalkoxy, hydroxyalkyl, aminoalkyl or alkylaminoalkyl;

A is a heterocyclic aromatic group selected from the group consisting of:

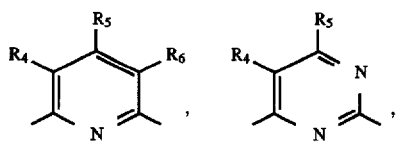

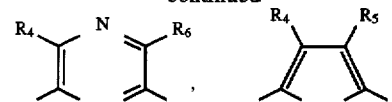

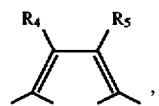

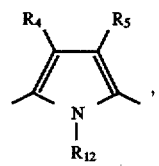

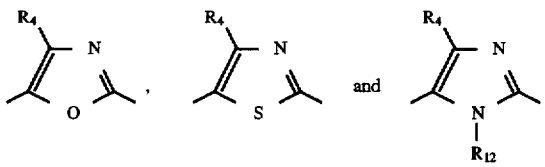

wherein $R_4$, $R_5$, and $R_6$ are each independently selected from the group consisting of H, lower alkyl, halogen, aryl, arylalkyl, aminoalkyl, aminoaryl, oxyalkyl, oxyaryl, or oxyarylalkyl;

$R_{12}$ is hydrogen, lower alkyl, hydroxy, aminoalkyl or alkylaminoalkyl, or a physiologically acceptable salt thereof; and (b) exposing said nucleic acid mixture to light to induce fluorescence of said compound of Formula (II); and (c) thereby detecting said DNA.

20. A method for the fluorescent detection of a microtubular structure comprising:

(a) contacting said microtubular structure with a compound according to Formula (II)

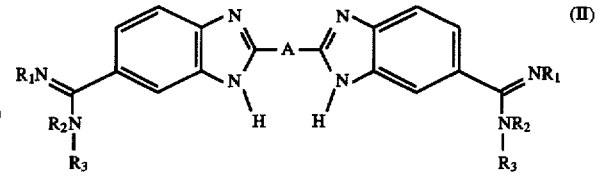

wherein:

$R_1$ and $R_2$ are each independently selected from the group consisting of H, lower alkyl, alkoxyalkyl, cycloalkyl, aryl, alkylaryl, hydroxyalkyl, aminoalkyl, or alkylaminoalkyl, or $R_1$ and $R_2$ together represent a $C_2$ to $C_{10}$ alkyl, hydroxyalkyl, or alkylene or $R_1$ and $R_2$ together are:

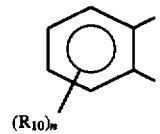

wherein n is from 1 to 3 and $R_{10}$ is H or —$CONHR_{11}NR_{15}R_{16}$, where $R_{11}$ is lower alkyl and $R_{15}$ and $R_{16}$ are each independently selected from the group consisting of H and lower alkyl;

$R_3$ is H, hydroxy, lower alkyl, cycloalkyl, aryl, alkylaryl, alkoxyalkyl, hydroxycycloalkyl, alkoxycycloalkoxy, hydroxyalkyl, aminoalkyl or alkylaminoalkyl;

A is a heterocyclic aromatic group selected from the group consisting of:

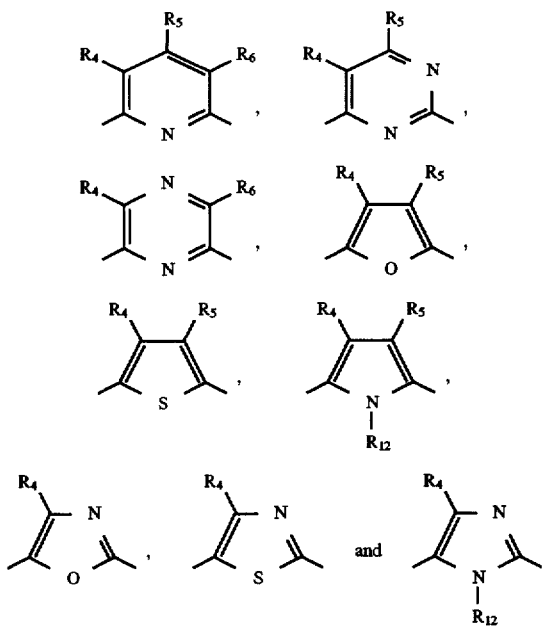

wherein R₄, R₅, and R₆ are each independently selected from the group consisting of H, lower alkyl, halogen, aryl, arylalkyl, aminoalkyl, aminoaryl, oxyalkyl, oxyaryl, or oxyarylalkyl;

R₁₂ is hydrogen, lower alkyl, hydroxy, aminoalkyl or alkylaminoalkyl, or a physiologically acceptable salt thereof; and (b) exposing said microtubular structure to light to induce fluorescence of said compound of Formula (II); and (c) thereby detecting said microtubular structure.

21. The method according to claim 20 wherein microtubular structure resides in a cell cytoskeleton.

22. A method for the simultaneous fluorescent detection of a first cellular structure and a second cellular structure in a cell, wherein said first cellular structure and said second cellular structure are different, said method comprising:

(a) contacting said cell with a first fluorescent compound and a second fluorescent compound, wherein said first fluorescent compound selectively binds to said first structure and said second compound selectively binds to said second structure, wherein said first fluorescent compound and said second fluorescent compound have different fluorescent emission spectra, wherein said second fluorescent compound is structurally different from said first fluorescent compound, and wherein each of said fluorescent compounds has a structure according to Formula (II)

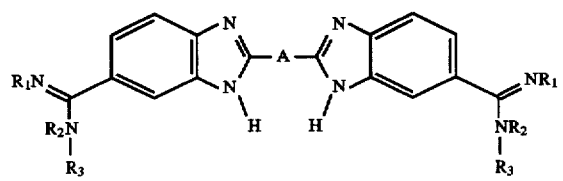

wherein:

R₁ and R₂ are each independently selected from the group consisting of H, lower alkyl, alkoxyalkyl, cycloalkyl, aryl, alkylaryl, hydroxyalkyl, aminoalkyl, or alkylaminoalkyl, or R₁ and R₂ together represent a C₂ to C₁₀ alkyl, hydroxyalkyl, or alkylene or R₁ and R₂ together are:

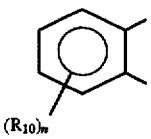

wherein n is from 1 to 3 and R₁₀ is H or —CONHR₁₁NR₁₅R₁₆, wherein R₁₁ is lower alkyl and R₁₅ and R₁₆ are each independently selected from the group consisting of H and lower alkyl;

R₃ is H, hydroxy, lower alkyl, cycloalkyl, aryl, alkylaryl, alkoxyalkyl, hydroxycycloalkyl, alkoxycycloalkoxy, hydroxyalkyl, aminoalkyl or alkylaminoalkyl;

A is a heterocyclic aromatic group selected from the group consisting of:

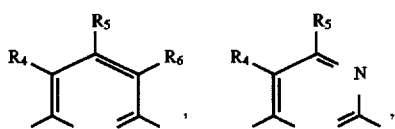

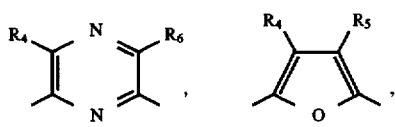

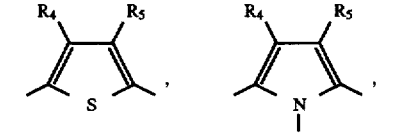

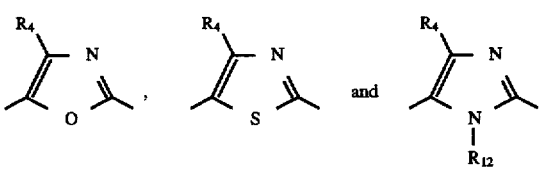

wherein R₄, R₅, and R₆ are each independently selected from the group consisting of H, lower alkyl, halogen, aryl, arylalkyl, aminoalkyl, aminoaryl, oxyalkyl, oxyaryl, or oxyarylalkyl;

R₁₂ is hydrogen, lower alkyl, hydroxy, aminoalkyl or alkylaminoalkyl, or a physiologically acceptable salt thereof; and (b) exposing said cell to light to induce fluorescence of both said first and second fluorescent compounds, so that said first cellular structure and said second cellular structure fluoresce at different fluorescent emission spectra, and (c) thereby simultaneously detecting said first and second cellular structures.

23. A method according to claim 22, wherein said first cellular structure and said second cellular structure are selected from the group consisting of DNA, RNA, and microtubular structures.

* * * * *